US009718864B2

(12) United States Patent
Luo et al.

(10) Patent No.: US 9,718,864 B2
(45) Date of Patent: Aug. 1, 2017

(54) αO-SUPERFAMILY CONOTOXIN PEPTIDE, PHARMACEUTICAL COMPOSITION AND USE THEREOF

(71) Applicant: HAINAN UNIVERSITY, Haikou Hainan (CN)

(72) Inventors: Sulan Luo, Haikou Hainan (CN); Dongting Zhangsun, Haikou Hainan (CN); Yong Wu, Haikou Hainan (CN); Xiaopeng Zhu, Haikou Hainan (CN); Yuanyan Hu, Haikou Hainan (CN); J. Michael McIntosh, Haikou Hainan (CN)

(73) Assignee: HAINAN UNIVERSITY, Haikou Hainan (CN)

( * ) Notice: Subject to any disclaimer, the term of this patent is extended or adjusted under 35 U.S.C. 154(b) by 0 days.

(21) Appl. No.: 14/407,770

(22) PCT Filed: Jun. 8, 2013

(86) PCT No.: PCT/CN2013/076967
§ 371 (c)(1),
(2) Date: Dec. 12, 2014

(87) PCT Pub. No.: WO2013/185572
PCT Pub. Date: Dec. 19, 2013

(65) Prior Publication Data
US 2015/0158921 A1    Jun. 11, 2015

(30) Foreign Application Priority Data
Jun. 15, 2012  (CN) .......................... 2012 1 0197589

(51) Int. Cl.
| C07K 14/435 | (2006.01) |
| C07K 14/00 | (2006.01) |
| C07K 1/00 | (2006.01) |
| G01N 33/50 | (2006.01) |
| G01N 33/68 | (2006.01) |
| G01N 33/94 | (2006.01) |
| A61K 38/00 | (2006.01) |

(52) U.S. Cl.
CPC .......... *C07K 14/43504* (2013.01); *C07K 1/00* (2013.01); *C07K 14/00* (2013.01); *G01N 33/5041* (2013.01); *G01N 33/6872* (2013.01); *G01N 33/944* (2013.01); *A61K 38/00* (2013.01); *C07K 2319/00* (2013.01); *C07K 2319/55* (2013.01); *G01N 2500/04* (2013.01); *G01N 2500/10* (2013.01)

(58) Field of Classification Search
None
See application file for complete search history.

(56) References Cited

U.S. PATENT DOCUMENTS 5,011,912 A * 4/1991 Hopp ...................... C07K 7/06
                                                  435/331
2004/0204362 A1  10/2004 Olivera et al.

FOREIGN PATENT DOCUMENTS

| CN | 1796412 A | 7/2006 |
| WO | 00/44769 A1 | 8/2000 |
| WO | 00/44776 A1 | 8/2000 |
| WO | 02/07756 A1 | 1/2002 |

OTHER PUBLICATIONS

Luo, S. et al., "alphaO-conotoxin GeXIVAWT precursor [Conus generalis]" NCBI Database Accession No. AFP87476.1 (Aug. 19, 2012) 1 page.
Luo, S. et al, "The application prospect of conotoxins produced by Hannan conus in treating pain and addiction" *Chinese Journal of Pharmacology and Toxicology* (Jun. 2012) pp. 439-440, vol. 26, No. 3, together with English-language abstract.
Luo, S. et al., "Diversity of the O-superfamily conotoxins from Conus miles" *Journal of Peptide Science* (Jan. 2007) pp. 44-53, vol. 13, No. 1.
Luo, S. et al., "RecName: Full=Conotoxin MiK41; Flags: Precursor [Conus miles]" NCBI Database Accession No. Q3YEG4.2 (Nov. 16, 2011) 3 pages.
Zhao, C. et al., "Recent advances in study of antinociceptive conotoxins" *Acta Pharmaceutica Sinica* (2009) pp. 561-565, vol. 44, No. 6, together with English-language abstract.
International Search Report dated Sep. 19, 2013 issued in International Application No. PCT/CN2013/076967.
Database Geneseq [Online] Mar. 6, 2008, "Conus 0-conotoxin, SEQ ID 39.", retrieved from EBI accession No. GSP:AOG49303 Database accession No. AOG49303.
Database Geneseq [Online] Mar. 6, 2008, "Conus 0-conotoxin protein fragment, SEQ ID 4.", retrieved from EBI accession No. GSP:AOG49268 Database accession No. AOG49268.

(Continued)

*Primary Examiner* — John Ulm
(74) *Attorney, Agent, or Firm* — Scully, Scott, Murphy & Presser, P.C.

(57) ABSTRACT

The present invention pertains to fields of biochemistry and molecular biology, relates to an αO-superfamily conotoxin peptide, pharmaceutical composition thereof, preparation method and use thereof. The present invention further relates to a propeptide of the conotoxin peptide, nucleic acid construct thereof, expression vector and transformed cell thereof, and fusion protein thereof. The present invention further relates to a method for blocking acetylcholine receptors as well as a use of the conotoxin peptide in the manufacture of a medicament. The new αO-superfamily conotoxin peptide of the present invention is capable of specifically blocking acetylcholine receptor (nAChRs) (e.g., α9α10 nAChR), and NMDA receptor (e.g., NR2C NMDAR), and has activity for treatment of neuralgia, addiction, and activity for treatment of chemotherapy of cancers, breast cancer, lung cancer, wound healing, epilepsia, ischemia, and thus is promising in the manufacture of analgesic, a medicament for treatment of addiction, and a tool drug for neuroscience.

10 Claims, 15 Drawing Sheets

(56) References Cited

OTHER PUBLICATIONS

Database Geneseq [Online] Mar. 6, 2008, "Conus 0-conotoxin coding sequence, SEQ ID 74.", retrieved from EBI accession No. GSN :AOG49338 Database accession No. AOG49338.
Bingmiao Gao et al: "Expression, renaturation and biological activity of recombinant conotoxin GeXIVAWT", Applied Microbiology and Biotechnology, vol. 97, No. 3, Jul. 24, 2012, pp. 1223-1230.
Supplementary European Search Report dated Nov. 6, 2015, issued in European Application No. EP 13 80 4082.
McIntosh, J.M. et al., "Alpha9 nicotinic acetylcholine receptors and the treatment of pain", Biochemical Pharmacology, (2009), vol. 78, pp. 693-702.
Satkunanathan, N. et al., "Alpha-conotoxin Vc1.1 alleviates neuropathic pain and accelerates functional recovery of injured neurones", Brain Research, (2005), vol. 1059, pp. 149-158.
Holtman, J.R. et al., The novel small molecule alpha9alpha10 nicotinic acetylcholine receptor antagonist ZZ-204G is analgesic, European Journal of Pharmacology, (2011), vol. 670, pp. 500-508.
Zheng, G. et al., "Discovery of non-peptide, small molecule antagonists of alpha9alpha10 nicotinic acetylcholine receptors as novel analgesics for the treatment of neuropathic and tonic inflammatory pain", Bioorganic & Medicinal Chemistry Letters, (2011), vol. 21, pp. 2476-2479.
Chikova, A. et al., "Naturally Occurring Variants of Human A9 Nicotinic Receptor Differentially Affect Bronchial cell Proliferation and Transformation", PLos One, (Nov. 2011), vol. 7, Issue 11, pp. 1-6.
Vincler, M. et al., "Molecular mechanism for analgesia involving specific antagonism alpha9alpha10 nicotinic acetylcholine receptors", PNAS, (Nov. 21, 2006), vol. 103, No. 47, pp. 17880-17884.
Sattler, R. et al., "Specific Coupling of NMDA Receptor Activation to Nitric Ocide Neurotoxicity by PSD-95 Protein", Science, (Jun. 11, 1999), vol. 284, pp. 1845-1848.
Lewis, R.J. et al., "Therapeutic Potential of Venom Peptides", Nature Reviews | Drug Discovery, (Oct. 2003), vol. 2, pp. 790-802.
Sheng, Z. et al., "The selectivity of conantokin-G for ion channel inhibition of NR2B subunit-containing NMDA receptors is regulated by amino acid residues in the S2 region of NR2B", Neuropharmacology, (2009), vol. 57, pp. 127-136.
Meldrum, B.S., "The role of glutamate in epilepsy and other CNS disorders", Neurology, (Nov. 1994), vol. 44, Suppl. 8, pp. S14-S23.
Ulas, J. et al., "Selective Increase of NMDA-Sensitive Glutamate Binding in the Striatum of Parkinson's Disease, Alzheimer's Disease, and Mixed Parkinson's Disease/Alzheimer's Disease Patients: An Autoradiographic Study", The Journal of Neuroscience, (Nov. 1994), vol. 14, No. 11, pp. 6317-6324.
Ozawa, S. et al., "Glutamate Receptors in the Mammalian Central Nervous System", Progress in Neurobiology, (1998), vol. 54, pp. 581-618.
Bisaga, A. et al., In search of a new pharmacological treatment for drug and alcohol addiction: N-methyl-D-aspartate (NMDA) antagonists, Drug and Alcohol Dependence, (2000), vol. 59, pp. 1-15.

* cited by examiner

α O-GeXIVA12    Connectivity   I–II, III–IV

TCRSSGRYCRSPYDRRRRYCRRITDACV (SEQ ID NO: 12)

α O-GeXIVA13    Connectivity   I–III, II–IV

TCRSSGRYCRSPYDRRRRYCRRITDACV (SEQ ID NO: 12)

α O-GeXIVA14    Connectivity   I–IV, II–III

TCRSSGRYCRSPYDRRRRYCRRITDACV (SEQ ID NO: 12)

αO-SUPERFAMILY CONOTOXIN PEPTIDE, PHARMACEUTICAL COMPOSITION AND USE THEREOF

TECHNICAL FIELD

The present invention pertains to fields of biochemistry and molecular biology, relates to an αO-superfamily conotoxin peptide, pharmaceutical composition, preparation method and use thereof. The present invention further relates to a propeptide of the conotoxin peptide, nucleic acid construct, expression vector and transformed cell and fusion protein thereof. The present invention further relates to a method for blocking nicotine acetylcholine receptors (nAChRs) or NMDA receptors (NMDAR) as well as a use of the conotoxin peptide in the manufacture of a medicament.

INCORPORATION BY REFERENCE OF SEQUENCE LISTING

The Sequence Listing in an ASCII text file, named as 31607 SequenceListing 8-11-16.txt of 20 KB, created on Aug. 22, 2016, and submitted to the United States Patent and Trademark Office via EFS-Web, is incorporated herein by reference.

BACKGROUND ART

Nicotine acetylcholine receptors (nAChRs) are membrane proteins that are prevalent in animal kingdom and have important physiological actions and clinical research significance, and they mediate many physiological functions of central and peripheral nervous systems, including learning, memory, response, analgesia and motion control. The nAChRs inactivate release of many neurotransmitters such as dopamine, noradrenaline, serotonin, γ-aminobutyric acid. It is confirmed that nAChRs are critical targets for screening medicines in diagnosis and treatment of a large group of important diseases, and these diseases include difficult miscellaneous diseases such as addiction, pains, cancers, amentia, Parkinson's disease, mental diseases, depression, myasthenia gravis. So far, there is no medicine for symptomatic treatment of these diseases. Common non-selective nAChR agonists such as nicotine could relieve symptoms of the above nerve diseases, but they have strong side-effects on heart and gastrointestinal tract and addiction. Hence, the key for treatment of the above diseases is to develop ligand medicines having high selectivity on various subtypes of nAChRs (Livett B G, Sandall D W, Keays D, Down J, Gayler K R, Satkunanathan N, Khalil Z. Therapeutic applications of conotoxins that target the neuronal nicotinic acetylcholine receptor. Toxicon. 2006, 48(7):810-829. Nicke, A., Wonnacott, S. & Lewis, R. J. Alpha-conotoxins as tools for the elucidation of structure and function of neuronal nicotinic acetylcholine receptor subtypes. European journal of biochemistry/FEBS 271, 2004, 2305-2319. Dani, J. A. & Bertrand, D. Nicotinic acetylcholine receptors and nicotinic cholinergic mechanisms of the central nervous system. Annual review of pharmacology and toxicology 2007, 47:699-729).

However, the precondition for developing such medicines is to obtain selective compounds capable of specifically binding various subtypes of nAChRs, which could be directly used as therapeutic medicines for relevant diseases, or as tool medicines for studying and identifying fine compositions and physiological functions of the various subtypes. In addition, in tissues of breast cancer and lung cancer, the activation of nicotine acetylcholine receptors on tumor cytomembrane could be blocked with medicines so as to effectively conduct early diagnosis or treatment of these catastrophic cancers.

The nAChRs have many subtypes assembled with different α and β subunits, and each subtype has distinct pharmacological features. Due to the lack of highly selective ligand compounds for various subtypes, many difficulties should be overcome in studying and illustrating fine structures and functions of various nAChRs subtypes.

Studies show that α9α10 nAChR is a new target of medicine for treatment of neuropathic pain (McIntosh, J. M.; Absalom, N.; Chebib, M.; Elgoyhen, A. B.; Vincler, M., Alpha9 nicotinic acetylcholine receptors and the treatment of pain. *Biochemical pharmacology* 2009, 78 (7), 693-702. Satkunanathan, N.; Livett, B.; Gayler, K.; Sandall, D.; Down, J.; Khalil, Z., Alpha-conotoxin Vc1.1 alleviates neuropathic pain and accelerates functional recovery of injured neurones. *Brain research* 2005, 1059 (2), 149-58.). The α9α10 nAChR blocking agent has function of alleviating neuropathic pain and accelerating recovery of injured neurons (Holtman, J. R.; Dwoskin, L. P.; Dowell, C.; Wala, E. P.; Zhang, Z.; Crooks, P. A.; McIntosh, J. M., The novel small molecule alpha9alpha10 nicotinic acetylcholine receptor antagonist ZZ-204G is analgesic. *European journal of pharmacology* 2011, 670 (2-3), 500-8. Zheng, G.; Zhang, Z.; Dowell, C.; Wala, E.; Dwoskin, L. P.; Holtman, J. R.; McIntosh, J. M.; Crooks, P. A., Discovery of non-peptide, small molecule antagonists of alpha9alpha10 nicotinic acetylcholine receptors as novel analgesics for the treatment of neuropathic and tonic inflammatory pain. *Bioorganic & medicinal chemistry letters* 2011, 21 (8), 2476-9). The α9α10 nAChR of keratinocyte plays an important role in pathological physiology process of wound healing (Chernyavsky, A. I.; Arredondo, J.; Vetter, D. E.; Grando, S. A., Central role of alpha9 acetylcholine receptor in coordinating keratinocyte adhesion and motility at the initiation of epithelialization. *Experimental cell research* 2007, 313 (16), 3542-55). Recent studies show that α9 nAChR subunit is overexpressed in breast cancer tissues. Variant of α9 subunit affects transformation and proliferation of bronchial cells, so the subunit has very important significance in treatment of lung cancer (Chikova, A.; Grando, S. A., Naturally occurring variants of human Alpha9 nicotinic receptor differentially affect bronchial cell proliferation and transformation. *PloS one* 2011, 6 (11), e27978.).

Surveys show pains including arthritis, neuralgia and sore pain affect ⅙ of population, among which neuralgia affects 4-8% of population. Existing methods for treatment of neuralgia mainly involve in local anaesthesia medication to block pain signal generated by peripheral nerves, nerve plexus, dorsal root nerves and sympathetic nervous system. However, these treatments merely have short-term analgesic effect, and cannot permanently control neuralgia. Many diseases may induce neuralgia, including cancers and chemotherapy of cancers, alcoholism, ischialgia, diabetes mellitus, prosopalgia, sclerosis, herpes zoster, mechanical injury and surgical injury, AIDS, head nerve paralysis, drug poisoning, industrial pollution poisoning, myeloma, multipoint neuralgia, chronic congenital esthesioneurosis, acute fierce spontaneous neuralgia, squeezing neuralgia, angiitis (vasculitis)/ischemia, uremia, children biliary liver disease, chronic respiratory disorder, complex neuralgia, multiple organ failure, sepsis/pyaemia, hepatitis, porphyria, avitaminosis, chronic liver diseases, primary biliary cirrhosis, hyperlipidemia, leprosy, Lyme arthritis, sensory perineuritis, allergies, etc.

Medicines using α9α10 nAChR as target for treatment of neuralgia can be delivered administered via intramuscular injection to exert analgesia effects (Vincler, M. Wittenauer, S. Parker, R. Ellison, M. Olivera, B. M. McIntosh, J. M. Molecular mechanism for analgesia involving specific antagonism of alpha9alpha10 nicotinic acetylcholine receptors. Proc Natl Acad Sci USA, 2006, 103 (47): 17880-4.), and are more convenient than the currently commercialized ω-CTx MVIIA analgesic, ziconotide. Ziconotide has to be directly delivered to spinal cord via a programmed pump in vivo, so its delivery route is very inconvenient, and the pump is very expensive. At present, it is merely available in developed countries in Europe and America, and can hardly be used in vast developing countries (Kress H G, Simpson K H, Marchettini P, Ver Donck A, Varrassi G. Intrathecal therapy: what has changed with the introduction of ziconotide. Pain Pract. 2009; 9(5):338-47. Burton A W, Deer T R, Wallace M S, Rauck R L, Grigsby E. Considerations and methodology for trialing ziconotide. Pain Physician. 2010; 13(1):23-33. Wallace M S, Rauck R L, Deer T. Ziconotide combination intrathecal therapy: rationale and evidence. Clin J Pain. 2010; 26(7):635-44).

Smoking addiction is caused by nicotine (nicotinamide) in tobacco, and its receptors in body are nicotine acetylcholine receptors (nAChRs) (Azam L, McIntosh J M. Alpha-conotoxins as pharmacological probes of nicotinic acetylcholine receptors. Acta Pharmacol Sin. 2009; 30(6): 771-783.). Many nAChRs subtypes are not only drug action targets for nicotine addiction, but also drug action targets for drug abuse of morphine, cocaine, etc.

NMDA receptor (N-methyl-D-aspartate receptor) is an important excitatory amino acid receptor in central nervous system, is a ligand-gated ion channel type receptor, and has broad physiological and pharmacological significance. NMDA receptor has significant physiological effects in development of nervous system, such as regulating neuronic survival, regulating structure development of neuronic dendrites and axons, and participating formation of synaptic plasticity; in addition, NMDA receptor also plays a pivotal role in formation of neuronal circuit. At focus of ischemia, NMDA receptor is activated, causing extracellular calcium ion entry, thereby resulting cell death (Twede, V. D., Miljanich, G., Olivera, B. M. & Bulaj, G. Neuroprotective and cardioprotective conopeptides: an emerging class of drug leads. *Current opinion in drug discovery & development* 2009, 12: 231-239). Studies via rat tests show that NMDA receptor is mainly distributed in central nervous system, such as brain, spinal cord; NMDA receptor is also found in peripheral nervous system, for example, NR3B is mainly expressed in motoneuron, while peripheral NMDA receptors play a very important role in facial muscle pain and edematization.

Studies show that NMDA receptors are very important receptors in processes such as learning, memory, pain, etc., and also attack and treatment targets for many nerve diseases, including refractory pains, drug and alcohol addiction, epilepsy, ischemia, Parkinson's disease, dementia, excitatory neuron death, etc. (Sattler, R. et al. Specific coupling of NMDA receptor activation to nitric oxide neurotoxicity by PSD-95 protein. *Science* (New York, N.Y.) 1999, 284, 1845-1848. Lewis, R. J. & Garcia, M. L. Therapeutic potential of venom peptides. *Nature reviews. Drug discovery,* 2003, 2: 790-802. Sheng, Z., Liang, Z., Geiger, J. H., Prorok, M. & Castellino, F. J. The selectivity of conantokin-G for ion channel inhibition of NR2B subunit-containing NMDA receptors is regulated by amino acid residues in the S2 region of NR2B. *Neuropharmacology,* 2009, 57, 127-136. Meldrum, B. S. The role of glutamate in epilepsy and other CNS disorders. *Neurology,* 1994, 44:S14-23. Ulas, J. et al. Selective increase of NMDA-sensitive glutamate binding in the striatum of Parkinson's disease, Alzheimer's disease, and mixed Parkinson's disease/Alzheimer's disease patients: an autoradiographic study. *The Journal of neuroscience,* 1994, 14, 6317-6324. Ozawa, S., Kamiya, H. & Tsuzuki, K. Glutamate receptors in the mammalian central nervous system. *Progress in neurobiology,* 1998, 54: 581-618. Bisaga, A. & Popik, P. In search of a new pharmacological treatment for drug and alcohol addiction: N-methyl-D-aspartate (NMDA) antagonists. *Drug and alcohol dependence,* 2000, 59: 1-15).

At present, conotoxin (CTx, conopeptide) generated in venom of conidae, a kind of carnivore mollusc living in tropical ocean, draws a lot of attentions, and is used for systematically studying and developing specific blocking agents for various subtypes of nAChRs.

Conotoxin (conopeptide, CTx) usually a neuropeptide toxin consisting of 7-50 amino acid residues and enriching with cysteine (Cys). Conotoxin can be classified into different gene families according to similarity of precursor protein endoplasmic reticulum targeting sequence and cysteine pattern. So far, all known conotoxins can be classified into 18 superfamilies, i.e., A, B, C, D, S, M, I1, I2, I3, J, L, O1, O2, O3, P, T, V, Y (Kaas Q, Yu R, Jin A H, Dutertre S, Craik D J (2012) ConoServer: updated content, knowledge, and discovery tools in the conopeptide database. Nucleic Acids Res 40: D325-330. Sulan Luo, Sean Christensen, Dongting Zhangsun, Yong Wu, Yuanyan Hu, Xiaopeng Zhu, Sandeep Chhabra, Raymond S. Norton, and J. Michael McIntosh. A Novel Inhibitor of α9α10 Nicotinic Acetylcholine Receptors from *Conus vexillum* Delineates a New Conotoxin Superfamily. PLoS ONE, 8(1): e54648 (1-10), 2013). Conotoxin (conopeptide) can be classified into pharmacological families α, ω, ||, δ and so on according to receptor target thereof, in which conotoxin of family α (α*-CTx) has function of blocking nicotine acetylcholine receptors (nAChRs); Conantokins as cysteine-free conopeptides have specific function of blocking N-methyl-D-aspartic acid receptor (NMDAR). According to receptor target type, each superfamily of conotoxin can further be classified into α, αA, κA (A-superfamily), ω, δ, κ, μO (O-superfamily), μ, Ψ, κM (M-superfamily), etc. (subtypes).

Conotoxins have special functions of specifically binding various ion channels in animal body. At present, conotoxins have drawn a lot of attentions and are systematically used for studying and developing specific blocking agents for various subtypes of nAChRs.

CONTENTS OF THE INVENTION

After intensive study and creative efforts, the inventors of the present invention find a new type of αO-superfamily conotoxin peptides. The inventors surprisingly find the αO-superfamily conotoxin peptides of the present invention can specifically block acetylcholine receptor and NMDA receptor, especially have the strongest activity of blocking α9α10 nAChR as the target of neuralgia medicines, breast cancer and lung cancer, and good application prospect in the manufacture of analgesics and medicines against addiction, epilepsy or cancers as well as tool medicines in neurosciences. Thus, the following invention is provided:

One aspect of the present invention relates to a polypeptide, which is or comprises one or more same or different amino acid sequences selected from any one of the following items (1) to (3):

(1) an amino acid sequence shown in any one of sequences of SEQ ID NO: 7-12;

(2) an amino acid sequence having at least 80%, preferably at least 85%, more preferably at least 90%, especially preferably at least 95%, most preferably at least 97% identity with the amino acid sequence of (1); or (3) an amino acid sequence different from the sequence of (1) in substitution, deletion, insertion and/or addition of 1-5, preferably 1-3, more preferably 1-2, most preferably 1 amino acid residue.

Wherein, SEQ ID NO: 7 or 8 is a wild type precursor peptide named as GeXIVAWT; SEQ ID NO: 9 is a mature peptide thereof.

SEQ ID NO: 10 or 11 is a mutant type precursor peptide named GeXIVA; SEQ ID NO: 12 is a mature peptide thereof.

The GeXIVA and wild type GeXIVAWT precursor peptides comprise 3 regions, i.e., a signal peptide, a propeptide and a mature peptide, their specific sequences and analysis thereof are described in Examples 1-2. The wild type mature peptide has 5 cysteines, different from all known conotoxins with pattern of even number of cysteines, and is a new αO-superfamily conotoxin. Since this toxin has the strongest activity of blocking α9α10 nAChR, it is named as αO-superfamily (αO-conotoxin).

For one purpose of the present invention, identity of two or more amino acid sequences is determined by BLAST2.0 Protein Database Query Program (Aaltschul et al., 1997, Nucleic Acid Research 25: 3389-3402) using the following parameters: blastall-p blastp-a4-e10-E0-v500-b250-I [query document]-d prot_all, in which -p refers to the name of program, -a refers to number of servers, -e refers to expectancy value, -E refers to cost of extension gap, -v refers to number of one-line description, -b refers to comparison number to be displayed, -I refers to query document, -d refers to database used for query.

Any one of amino acid sequence differences between the amino acid sequence of homologic polypeptide and SEQ ID NO: 1-4 may lie in substitution, insertion addition and/or deletion of one or more, preferably 1-5, more preferably 1-3, especially preferably 1-2, most preferably 1 amino acid residue. Preferably, the change of amino acid is small change of property, i.e., it is a conservative amino acid substitution, a deletion of small fragment which usually is a deletion of 1 to about 5, preferably 1-3, more preferably 1 amino acid, a small amino or carboxyl terminal extension such as a methionine residue added to amino terminal, a small linker peptide having up to about 20-25 residues, that does not significantly affect folding and/or activity of protein; or a small extension such as polyhistidine fragment, epitope, binding domain contributing to purification via changing net charge or other function.

Without any theoretical restriction, an example of conservative substitution is a substitution within basic amino acids (arginine, lysine, and histidine), acidic amino acids (glutamic acid and aspartic acid), polar amino acids (glutamine and asparagine), hydrophobic amino acids (leucine, isoleucine and valine), amino acids with similar shape (between arginine and serine), amino acids differing from cysteine codon in one base (cysteine, arginine, serine, tryptophane, glycine, tyrosine, and phenylalanine), aromatic amino acids (phenylalanine, tryptophane and tyrosine), and small amino acids (glycine, alanine, serine, threonine and methionine). The amino acid substitutions usually not changing specific activity are known in the art, and are described in, for example, "Proteins", H. Neurath and R. L. Hill, 1979, Academic Press, New York. The commonest substitutions are Ala/Ser, Val/Ile, Asp/Glu, Thr/Ser, Ala/Gly, Ala/Thr, Ser/Asn, Ala/Val, Ser/Gly, Arg/Ser, Cys/Ser, Arg/Cys, Arg/Ala, Tyr/Phe, Ala/Pro, Lys/Arg, Asp/Asn, Leu/Ile, Leu/Val, Ala/Glu and Asp/Gly, etc. and substitutions vice versa.

The present invention further comprises fused polypeptides or lysable fused polypeptides in which the N-terminal and/or C-terminal of αO-conotoxin is fused with other peptide/polypeptide. The technology for generating fused polypeptides is known in the art, comprising linking a coding sequence coding the peptide of the present invention with a coding sequence coding the other peptide/polypeptide so that they are in one reading frame and the expression of the fused polypeptide is controlled by the same promoter and terminator.

In the polypeptide according to any item of the present invention, at the N-terminal of SEQ ID NO:12, the $1^{st}$ cysteine and the $2^{nd}$ cysteine form a disulfide bond, and the $3^{rd}$ cysteine and the $4^{th}$ cysteine form a disulfide bond; or the $1^{st}$ cysteine and the $3^{rd}$ cysteine form a disulfide bond, and the $2^{nd}$ cysteine and the $4^{th}$ cysteine form a disulfide bond; or the $1^{st}$ cysteine and the $4^{th}$ cysteine form a disulfide bond, and the $2^{nd}$ cysteine and the $3^{rd}$ cysteine form a disulfide bond; specifically, the carboxyl terminal of the polypeptide is a free C-terminal, or amidated.

The polypeptide of the present invention is conotoxin peptide; and specifically, is αO-conotoxin.

The conotoxin peptide can be extracted from *Conus C. generalis* produced in Hainan Province of China, or a mature peptide sequence derived from its gene; or can be an amino acid of chemical synthesis (e.g., the method of Example 3); or a polypeptide obtained by expressing its nucleotide via genetic recombination (the nucleotide sequence can be prepared by the method of Examples 1-2 or by directly artificial synthesis); or by referring to the following method:

Another aspect of the present invention relates to a method for preparing any one of the peptides of the present invention, comprising the following steps:

1) synthesizing a linear polypeptide by ABI Prism 433a polypeptide synthesizer or by manual method, in which side-chain protecting groups of Fmoc amino acid are: Pmc (Arg), Trt (Cys), But (Thr, Ser, Tyr), OBut (Asp), Boc (Lys); cysteine is protected with Trt or Acm as protecting group, disulfide bonds are respectively formed in a site-directed manner between corresponding cysteines; or all cysteines randomly form disulfide bonds with Trt protecting group via one-step method of oxidation and folding.

2) cutting the linear polypeptide of step 1) from resin, using ice-ether to precipitate and wash and recover a crude product of linear polypeptide, and using a preparative reversed phase HPLC C18 column (Vydac) for purification;

3) subjecting the product obtained in step 2) to two- or one-step oxidative folding.

Another aspect of the present invention relates to a polynucleotide which coding an amino acid sequence of the polypeptide of any one of items of the present invention.

The polynucleotide of any one of items of the present invention comprises one or more same or different nucleotide sequences selected from any one of the following items (1) to (3):

(1) a nucleotide sequence as shown in any one of sequences of SEQ ID NO: 1-6;

(2) a complementary sequence of any one of sequences of SEQ ID NO: 1-6; or (3) a nucleotide sequence capable of hybridizing with the nucleotide sequence of (1) or (2) under a stringent condition.

SEQ ID NO: 1-6 separately are encoding sequences of SEQ ID NO: 7-12.

Wherein, SEQ ID NO: 1 or 2 encodes a wild type precursor peptide named as GeXIVAWT; SEQ ID NO: 3 encodes a mature peptide thereof.

SEQ ID NO: 4 or 5 encodes a mutant type precursor peptide named as GeXIVA; SEQ ID NO: 6 encodes a mature peptide thereof.

The specific sequences of SEQ ID NO: 1-6 and analysis thereof are described in Examples 1-2.

As for hybridization between polynucleotides, reference can be found in many documents in the art, including, for example, Molecular Cloning: A Laboratory Manual, Edition 2, Sambrook, etc., Cold Spring Harbor Laboratory Press, Cold Spring, 1989. The hybridization can use stringent conditions of various degrees, for example, moderately stringent conditions, moderately-highly stringent conditions, or highly stringent conditions. The more stringent the conditions are, the higher complementary degree required for forming double helix. The stringent degree can be controlled via temperature, probe concentration, probe length, ion strength, time, etc. For double-stranded DNA, the hybridization is performed at a temperature 20-25° C. lower than the melting temperature [Tm] of DNA heterozygote in 6×SSPE, 5×Denhardt's solution, 0.1% SDS, 0.1 mg/ml denatured DNA overnight. The washing is usually performed as follows: at Tm-20° C. in 0.2×SSPE, 0.1% SDS, once, 15 minutes (washing under moderately stringent condition).

Further another aspect of the present invention relates to a primer pair, which is or comprises a nucleotide sequence as shown in SEQ ID NO: 13 and SEQ ID NO: 14. The primer pair can be used for PCR amplification, to obtain the polynucleotide sequence as shown in SEQ ID NO: 1 or SEQ ID NO: 2.

Further another aspect of the present invention relates to a nucleic acid construct, which comprises the polynucleotide of any one of items of the present invention.

Further another aspect of the present invention relates to a recombinant expression vector, which comprises the nucleic acid construct of the present invention; specifically, said recombinant vector is recombinant pET22b(+) vector.

Further another aspect of the present invention relates to a transformed cell, which comprises the recombinant expression vector of the present invention; specifically, said transformed cell is a transformed Sf9 cell.

Further another aspect of the present invention relates to a fusion protein, which comprises the polypeptide of any one of items of the present invention.

Further another aspect of the present invention relates to a pharmaceutical composition, which comprises the polypeptide of any one of items of the present invention, or the fusion protein of the present invention; optionally, which further comprises a pharmaceutically acceptable carrier or excipient.

Further aspect of the present invention relates to a method for blocking acetylcholine receptor and NMDA receptor, comprising the step of using an effective amount of the polypeptide or fusion protein of any one of items of the present invention; specifically, said acetylcholine receptor is α9α10 acetylcholine receptor, or other acetylcholine receptor subtype and NMDA receptor.

Further aspect of the present invention relates to a method for screening an acetylcholine receptor inhibitor and a NMDA receptor or determining the subtype of acetylcholine receptor and NMDA receptor, the method comprising: a step of contacting an acetylcholine receptor or NMDA receptor subtype with the polypeptide or fusion protein of any one of items of the present invention in the presence or absence of a candidate compound; specifically, said acetylcholine receptor is α9α10 acetylcholine receptor; or said NMDA receptor is NR2C NMDA receptor. When αO-conotoxin GeXIVA can specifically block α9α10 acetylcholine receptor under very low concentration, it can be determined that the acetylcholine receptor is α9α10 subtype acetylcholine; or when αO-conotoxin GeXIVA can specifically block NR2C NMDA receptor under relatively lower concentration, it can be determined that the NMDA receptor is NR2C NMDA receptor.

Further aspect of the present invention relates to a use of the polypeptide or fusion protein of any one of items of the present invention in blocking acetylcholine receptor and NMDA receptor; specifically, said acetylcholine receptor is α9α10 acetylcholine receptor, or other acetylcholine receptor subtype; or NR2C NMDA receptor or other subtype.

Further aspect of the present invention relates to a use of the polypeptide or fusion protein of any one of items of the present invention in the manufacture of a medicament or reagent for blocking acetylcholine receptor and NMDA receptor; specifically, said acetylcholine receptor is α9α10 acetylcholine receptor, and NR2C NMDA receptor.

Further aspect of the present invention relates to a use of the polypeptide or fusion protein of any one of items of the present invention in the manufacture of a medicament for treatment or prophylaxis of nervous system disease, such as neuralgia, breast cancer, lung cancer, addiction, epilepsy, ischemia, Parkinson's disease, dementia, or excitatory neuron death, or a use in the manufacture of a drug for killing a pest (e.g., *Spodoptera Frugiperda*), analgesia, smoking cessation, or addiction treatment; specifically, said neuralgia is included by the following causes: cancers and chemotherapy of cancers, alcoholism, ischioneuralgia, diabetes mellitus, prosopalgia, sclerosis, herpes zoster, mechanical injury and surgical injury, AIDS, head nerve paralysis, drug poisoning, industrial pollution poisoning, lymphatic neuralgia, myeloma, multipoint motor neuralgia, chronic congenital esthesioneurosis, acute spontaneous neuralgia, squeezing neuralgia, angiitis, vasculitis, ischemia, uremia, children biliary liver disease, chronic respiratory disorder, complex neuralgia, multiple organ failure, sepsis/pyaemia, hepatitis, porphyria, avitaminosis, chronic liver diseases, primary biliary cirrhosis, hyperlipidemia, leprosy, Lyme arthritis, sensory perineuritis, allergies, etc.

Further aspect of the present invention relates to a method for treatment and/or prophylaxis and/or adjuvant therapy of nervous system diseases such as neuralgia, breast cancer, lung cancer, addiction, epilepsy, ischemia, Parkinson's disease, dementia, or excitatory neuron death, or a method for killing a pest (e.g., *Spodoptera Frugiperda*), analgesia, smoking cessation, or addiction treatment, comprising the step of administering an effective amount of the polypeptide (conotoxin peptide or propeptide thereof) or fusion protein or the present invention or the pharmaceutical composition of the present invention; specifically, said neuralgia is induced by the following reasons: cancers and chemotherapy of cancers, alcoholism, ischioneuralgia, diabetes mellitus, prosopalgia, sclerosis, herpes zoster, mechanical injury and surgical injury, AIDS, head nerve paralysis, drug poisoning, industrial pollution poisoning, lymphatic neuralgia, myeloma, multipoint motor neuralgia, chronic congenital esthesioneurosis, acute spontaneous neuralgia, squeezing neuralgia, angiitis, vasculitis, ischemia, uremia, children biliary liver disease, chronic respiratory disorder, complex neuralgia, multiple organ failure, sepsis/pyaemia, hepatitis, porphyria, avitaminosis, chronic liver diseases, primary biliary cirrhosis, hyperlipidemia, leprosy, Lyme arthritis, sensory perineuritis, allergies, etc.

The conotoxin peptide of the present invention can exert effects by binding α9α10 acetylcholine receptor (nAChR) or/and NR2C NMDA receptor, have analgesia effect, can be used for studying, diagnosis and treatment of nervous system diseases such as neuralgia, breast cancer, lung cancer, Parkinson's disease, dementia, addiction, epilepsy, ischemia, and as a useful molecular probe in studying. Affinity of different α CTx to vertebrate receptor is very diverse, for example, in several orders of magnitude. Such diversity in germ lines makes α CTx be used a useful probe for studying phylogenesis of vertebrates, or be used as molecular probe for determining nAchR subtype. They are candidate drugs, primary drugs and therapeutic drugs in developing new drugs.

The terms used in the present invention are explained as follows.

Neuralgia

The polypeptide of the present invention relates to a use for treatment of various neuralgias. Neuralgia is a pain caused by a primary or secondary lesion or a functional disorder or a transient disorder of peripheral or central nervous system, manifesting in spontaneous pain, sense hypersensitivity, etc. Neuralgia may be caused by many diseases, including cancers and chemotherapy of cancers, alcoholism, ischioneuralgia, diabetes mellitus, prosopalgia, sclerosis, herpes zoster, mechanical injury and surgical injury, AIDS, head nerve paralysis, drug poisoning, industrial pollution poisoning, myeloma, multipoint neuralgia, chronic congenital esthesioneurosis, acute fierce spontaneous neuralgia, squeezing neuralgia, angiitis (vasculitis)/ischemia, uremia, children biliary liver disease, chronic respiratory disorder, complex neuralgia, multiple organ failure, sepsis/pyaemia, hepatitis, porphyria, avitaminosis, chronic liver diseases, primary biliary cirrhosis, hyperlipidemia, leprosy, Lyme arthritis, sensory perineuritis, allergies, etc.

Nucleic Acid Construct

The present invention further relates to a nucleic acid construct comprising the nucleic acid sequence of the present invention and 1 or more regulatory sequences operably linked thereto, the regulatory sequences under compatible conditions thereof can guide an encoding sequence to express in a suitable host cell. The expression should be understood to comprise any steps relating to produce polypeptide, including but not limited to transcription, modification after transcription, translation, modification and secretion after translation.

In the text, "nucleic acid construct" is defined as a single chain or double chain nucleic acid molecule, which is separated from natural gene, or comprises nucleic acid fragments combined and collocated in non-natural manner via modification. When the nucleic acid construct comprises all regulatory sequences necessary for expressing the coding sequence of the present invention, the term "nucleic acid construct" has the same meaning of expression cassette. In the text, the term "coding sequence" is defined as a part of nucleic acid sequence for directly determining amino acid sequence of protein product. The boundaries of coding sequence usually are determined with ribosome bind site (corresponding to prokaryotic cell) closely adjacent to mRNA 5' terminal open reading frame upstream and transcription termination sequence closely adjacent to mRNA 3' terminal open reading frame downstream. Coding sequence can comprise but is not limited to DNA, cDNA and recombinant nucleic acid sequence.

The separated nucleic acid sequence encoding the peptide of the present invention can be manipulated with many manners so as to express the peptide. Depending on expression vector, the nucleic acid sequence can be processed before insertion into the vector if necessary. The technology of modifying nucleic acid sequence using recombinant DNA method is well known in the art.

The term "regulatory sequences" in the text is defined as all components necessary for or contributive to the expression of the peptide of the present invention. Each regulatory sequence naturally exists in or is extraneously added to the nucleic acid sequence coding the polypeptide. These regulatory sequences include but are not limited to leader sequences, polyadenylate sequences, propeptide sequences, promoters, signal sequences and transcription terminators. The lowest limit is that the regulatory sequences should comprise promoters and termination signals for transcription and translation. In order to introduce a specific restriction site to link the regulatory sequence to the coding region of nucleic acid sequence coding the polypeptide, a regulatory sequence with a connector can be provided. The term "operably linking" in the text refers to a conformation in which the regulatory sequence is at a suitable position of coding sequence corresponding to DNA sequence so that the regulatory sequence guides the expression of the polypeptide.

The regulatory sequence can be any suitable promoter sequence, i.e., a nucleic acid sequence that can be recognized by a host cell expressing nucleic acid sequence. The promoter sequence comprises a transcriptional regulatory sequence mediating polypeptide expression. The promoter can be any nucleic acid sequence having transcription activity in a selected host cell, including mutant, truncated and hybridized promoters, and can be obtained from a gene coding extracellular or intracellular polypeptide homologous or heterogeneous to host cell.

The regulatory sequence can further be a suitable transcription termination sequence, i.e., a sequence capable of being recognized by host cell so as to terminate transcription. The termination sequence is operably linked to 3' terminal of the nucleic acid sequence coding the polypeptide. Any terminators having such function in a selected host cell can be used in the present invention.

The regulatory sequence can further be a suitable leader sequence, i.e., a mRNA untranslated region very important for translation of host cell. The leader sequence is operably linked to 5' terminal of the nucleic acid sequence coding the polypeptide. Any leader sequence capable of exerting function in a selected host cell can be used in the present invention.

The regulatory sequence can further be a coding region of signal peptide, and the region codes an amino acid sequence linked to amino terminal of polypeptide, and can lead the coded polypeptide into cell secretion route. The 5' terminal of coding region of nucleic acid sequence can naturally contain a signal peptide coding region consistent to translation reading frame and naturally linked to a coding region of secreted polypeptide. Or, the 5' terminal of coding region can contain extraneous signal peptide coding region relative to the coding sequence. When the coding sequence does not contain signal peptide coding region under normal condition, an extraneous signal peptide coding region may be added. Or, an extraneous signal peptide coding region can be used to simply substitute a natural signal peptide coding region so as to enhance secretion of polypeptide. However, any signal peptide coding region capable of leading an expressed polypeptide to enter into a secretion route of a used host cell can be used in the present invention.

The regulatory sequence can further be a propeptide coding region, the region codes an amino acid sequence at amino terminal of polypeptide. The obtained polypeptide is called as proenzyme or propolypeptide. The propolypeptide usually has not activity, and can be transformed into a mature active polypeptide by cutting propeptide from propolypeptide via catalysis or self catalysis.

When the amino terminal of polypeptide has both signal peptide and propeptide, the propeptide is close to the amino terminal, while the signal peptide is close to the amino terminal of the propeptide.

It may also be necessary to add a regulatory sequence capable of regulating polypeptide expression according to growth conditions of host cells. Examples of regulatory system are systems capable of responding to a chemical or physical stimulation (included in a condition having a regulatory compound) so as to open or close gene expression. Other examples of the regulatory sequence are regulatory sequences capable of amplifying gene. In these examples, the nucleic acid sequence coding polypeptide should be operably linked to the regulatory sequence.

Expression Vector

The present invention further relates to a recombinant expression vector comprising the nucleic acid sequence of the present invention, a promoter and a terminal signal for transcription and translation. The above nucleic acids and regulatory sequences could be linked together to prepare a recombinant expression vector, and the vector can comprise 1 or more convenient restriction sites so that the nucleic acid sequence coding the polypeptide can be inserted or substituted at these sites. Or, the nucleic acid sequence or a nucleic acid construct comprising the sequence can be inserted into a suitable expression vector to express the nucleic acid sequence of the present invention. When the expression vector is prepared, the coding sequence can be in the vector so as to operably link to a suitable expression regulatory sequence.

The recombinant expression vector can be any vector (e.g., plasmid or virus) capable of performing recombinant DNA operation and expressing nucleic acid. The selection of vector usually depends on compatibility of vector and host cell into which the vector is introduced. The vector can be a linear or closed plasmid.

The vector can be an autonomously replicating vector (i.e., an extrachromosomal complete construct, which can be replicated independent of chromosome), such as plasmid, extrachromosomal component, minute chromosome, or artificial chromosome. The vector can comprise any mechanism ensuring self-replication. Or, the vector is a vector that is integrated into genome and replicated together with the chromosome into which it is integrated when the vector is introduced into a host cell. In addition, the used vector can be a single vector or plasmid, or generally contained 2 or more vectors or plasmids of total DNA to be introduced into host cell genome, or a transposon.

Preferably, the vector of the present invention comprises 1 or more selective markers convenient for selecting transformed cells. The selective marker is such a gene which product provides a resistance against a biocide, a resistance against a heavy metal, or provides an auxotroph prototrophy. Examples of bacterial selective markers are dal gene of *bacillus subtilis* or *bacillus licheniformis*, or resistance makers including antibiotics such as ampicillin, kanamycin, chloromycetin, or tetracycline.

Preferably, the vector of the present invention comprises components ensuring the vector to be stably integrated into genome of host cell, or ensuring the vector to be autonomously replicated independent of cell genome in cell.

As to autonomous replication, the vector can further comprise a replication organ so that the vector can be autonomously replicated in host cell. The replication organ can have a mutation that makes it a temperature-sensitive type in the host cell (see: for example, fEhrlich, 1978, National Academy of Sciences, 75:1433).

More than one copy of the nucleic acid sequence of the present invention can be inserted into a host cell to increase the output of gene product. The number of copies of the nucleic acid sequence can be increased by inserting at least one additional copy of the sequence into genome of host cell, or by inserting the nucleic acid sequence together with an amplification selective marker, culturing cells in the presence of a suitable selective reagent, picking out cells that have selective marker gene for copy amplification and thus have additional copies of the nucleic acid.

The steps for linking the above components to construct the recombinant expression vector of the present invention are well known in the art (see: for example, Molecular Cloning: A Laboratory Manual, Edition 2, Sambrook, etc., Cold Spring Harbor Laboratory Press, Cold Spring, 1989).

Host Cells

The present invention further relates to a recombinant host cell comprising the nucleic acid sequence of the present invention for recombination production of polypeptide. A vector comprising the nucleic acid sequence of the present invention can be introduced into a host cell so that the vector is maintained in form of the above chromosomal integrated body or self-replicable extrachromosomal vector. The term "host cell" covers any offspring that are different from parent cells due to mutation during replication period. The selection of host cell mainly depends on polypeptide coding gene and source thereof.

The host cell can be a prokaryotic cell or an eukaryotic cell, for example, a bacterium or yeast cell. The vector can be introduced into the host cell by a technology well known in the art.

Preparation Method

The present invention further relates to a method for recombination production of the peptide of the present invention, the method comprising: (a) culturing a host cell having a nucleic acid construct under conditions suitable to produce the peptide, the nucleic acid construct comprising a nucleic acid sequence encoding the peptide; and (b) recovering the peptide.

In the preparation method of the present invention, the cell is cultured in a nutrient medium suitable for polypeptide production by a method known in the art. For example, the cell is cultured by shake-flask culture, laboratory culture, small or large scale fermentation in industrial fermentation tank (including continuous, batch, batch charging or solid state fermentation) in a suitable culture medium under conditions allowing polypeptide expression and/or separation. The culture can be carried out with steps known in the art in a suitable culture medium containing carbon source and nitrogen source and inorganic salt. The suitable culture medium can be provided by suppliers or prepared according to a composition known in the art (for example, those in the catalogue of American Type Culture Collection). If the polypeptide is secreted in the culture medium, the polypeptide can be directly recovered from the culture medium. If the polypeptide is secreted out, it can be recovered from cell lysate.

The produced polypeptide can be recovered by a method known in the art. For example, the polypeptide can be recovered from the culture medium by conventional steps (including but not limited to centrifugation, filtration, spray drying, evaporation or precipitation).

The polypeptide of the present invention can be purified by known steps in the art, and these steps include but are not limited to chromatography (e.g., ion exchange chromatography, affinity chromatography, hydrophobic interaction chromatography, chromatofocusing, and size exclusion chromatography), HPLC, electrophoresis (e.g., preparative isoelectric focusing), differential solubility (e.g., ammonium sulfate precipitation), SDS-PAGE or extraction (see: for example, Protein Purification, edited by J. C. Janson and Lars Ryden, VCH Publishers, New York, 1989).

Method and Preparation for Controlling Pests

Many methods known by those skilled in the art can be used for controlling pests with the conotoxin peptide or polynucleotide of the present invention. These methods comprise, for example, applying a recombinant microorganism to pests (or their locus), and transforming a plant with a gene encoding the conotoxin peptide of the present invention. The transformation can be carried out by conventional methods known by those skilled in the art. Necessary substances for such transformation are disclosed here or can be readily obtained via other routes by those skilled in the art.

The preparation containing the conotoxin peptide or the recombinant microorganism of the polynucleotide of the present invention can be applied to soil. The prepared product can further be used for seed coating or root treatment or application on whole plant in later period of plant growth cycle. The preparation can comprise a diffusion-thickening adjuvant, a stabilizing agent, other pesticide additives, or a surfactant. A liquid preparation can be aqueous or nonaqueous, and used in form of foam, gel, suspension, emulsible concentrate. Components can comprise rheological agents, surfactants, emulsifying agents, dispersing agents, or polymers.

Those skilled in the art understand that pesticide can have a widely changing concentration due to nature of specific preparations, especially, it can be a concentrate or directly used. Pesticide can be in an amount of at least 1% by weight, or 100% by weight. Dry preparation usually has about 1-95% by weight of pesticide, while liquid preparation usually has a solid content of about 1-60% by weight in liquid phase. A preparation containing cells usually have about $10^2$ to about $10^4$ cells/mg. These preparations can be applied in an amount of 50 mg (liquid or dry) to 1 kg per hectare. The preparations can be applied to pest environment such as soil and plant by spraying, scattering, splashing.

Pharmaceutical Composition

The present invention further relates to a pharmaceutical composition comprising the peptide of the present invention and a pharmaceutically acceptable carrier and/or excipient. The pharmaceutical composition can be used for studying, diagnosis, alleviation or treatment of diseases or disorders relating to neuralgia, breast cancer, lung cancer, amentia, addiction, pain, Parkinson's disease, mental disorders, depression, myasthenia gravis, epilepsy, ischemia, etc. In an embodiment, a pharmaceutical composition comprising a therapeutically effective amount of the peptide of the present invention is prepared and administered in a way facilitating medicinal application, and clinical state of individual patient, delivery site, administration method, administration schedule and other factors known by doctor should also be considered. Thus, "effective amount" for the purpose in the text is determined with considerations in these aspects.

A pharmaceutical composition comprising a therapeutically effective amount of the peptide of the present invention can be administered parenterally, orally, intracisternally, intrathecally. "Pharmaceutically acceptable carrier" refers to a nontoxic solid, semi-solid or liquid filler, diluent, capsule material or any type of formula assistants. The term "parenterally" in the text refers to administration manners including intravenous, intramuscular, intraperitoneal, intrathoracic, subcutaneous, intrathecal, and intra-articular injection or infusion. The polypeptide of the present invention can also be administered via a sustained-release system.

The present invention further relates to a pharmaceutical composition for specifically blocking nAChRs and/or NMDA receptor.

The conotoxin peptide of the present invention can be used as a probe for studying phylogenesis of animal nAChRs and/or NMDARs; as a probe for determining different subtypes of nAChRs or/and NMDARs; as a molecular model for designing new drug; as a tool drug and treatment drug for studying and diagnosis of neurological diseases such as Parkinson's diseases, dyspraxia, schizophrenia, epilepsy, ischemia; a candidate drug for treatment of neuralgia, addiction, breast cancer, lung cancer, small cell lung cancer, epilepsy, ischemia, or as a polypeptide pesticide for developing new type of biopesticide.

Beneficial Effects of the Invention

The αO-conotoxin peptide of the present invention can specifically block acetylcholine receptors (nAChRs) and NMDA receptor, and has analgesia activity and functions for inhibiting growth of breast cancer and lung cancer cells, as well as functions for treatment of addiction, addiction, epilepsy and ischemia.

BRIEF DESCRIPTION OF THE DRAWINGS

Notation: when sources of various nAChRs and NMDA receptor subtypes are not given in the drawings, they are all corresponding rat receptors, and the sources of rat receptor types are omitted in the legends and drawings.

SPECIFIC MODELS FOR CARRYING OUT THE INVENTION

Figures 1, 2:
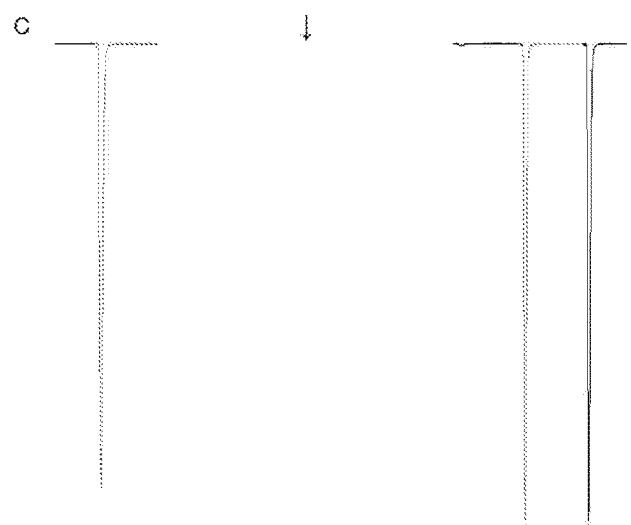
FIG. 1: shows αO-GeXIVA mature peptide sequence (SEQ ID NO: 1) and isomers having 3 possible disulfide bond linkage ways, in which GeXIVA12 has disulfide bond linkage ways of I-II, III-IV; GeXIVA13 has disulfide bond linkage ways of I-III, II-IV; GeXIVA14 has disulfide bond linkage ways of I-IV, II-III.
FIG. 2: shows in A the effects of 33 nM αO-GeXIVA12 on electric current of α9α10 nAChR. In diagram A, "C" refers to a control electric current, the arrow indicates the current track (~0 nA) formed by the first Ach pulse with Ach pulse time of 1 s after 33 nM αO-GeXIVA12 was incubated for 5 minutes; ordinate refers to current strength in unit of nA, abscissa refers to cumulative time in unit of ms, the interval time between any of 2 adjacent current tracks is 60 s before and after incubation. 33 nMαO-GeXIVA12 totally blocks α9α10 nAChR current, and elution is very rapid. In the figure, B, C, D separately refers to concentration dose-response curves of 3 isomers, αO-GeXIVA12, αO-GeXIVA13, αO-GeXIVA14, versus α9α10 nAChR. In the diagrams B, C, D, abscissa refers to log value (Log [Toxin Concentration]M) of molar concentration (M) of αO-GeXIVA isomer; ordinate refers to does-response percentage (% Response), which is a ratio percentage of acetylcholine receptor current to control current under action of toxin of corresponding concentration, each dose-response percentage is a mean value (mean) of data of 6-12 *Xenopus* oocytes, and the curve shows standard error (SEM) at the same time.
Figure 2:
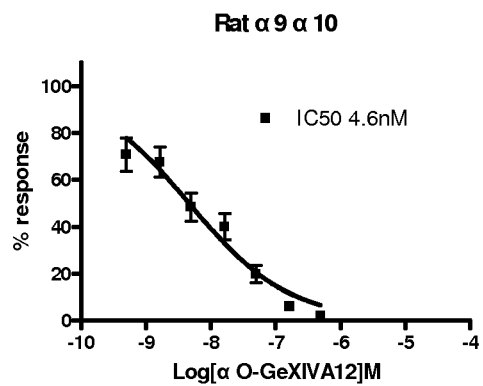
Figure 2:
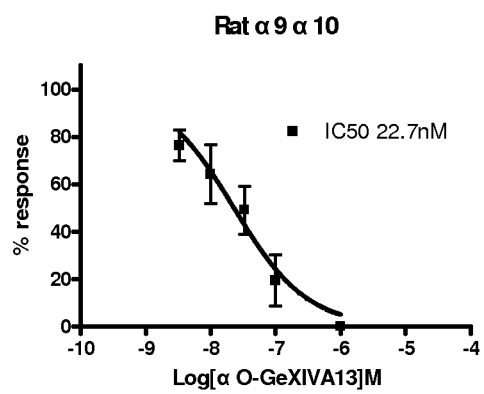
Figure 2:
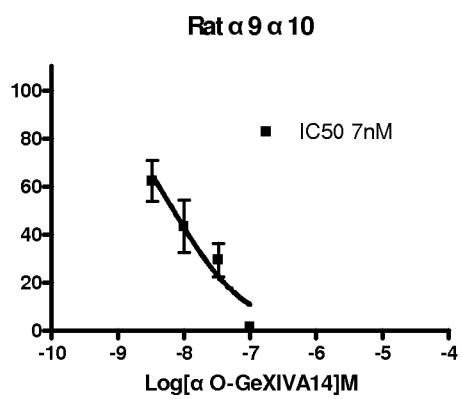

The embodiments of the present invention are illustrated in conjunction with examples as follows. Those skilled in the art would understand the following examples are merely used for illustrating the present invention, rather than limiting the scope of the present invention. The specific technologies or conditions that are not given in the specification are carried out according to the technologies or conditions described in the documents in the art (e.g., Molecular Cloning: A Laboratory Manual, Edition 3, J. Sambrook, etc., translated by HUANG Peitang, etc., Science Press), corresponding reference documents or specifications. All reagents or instruments which manufacturers are not given are commercially available conventional products.

Example 1

Cloning and Sequence Analysis of New αO-Superfamily Conotoxin Gene Wild Type (GeXIVAWT)

*Conus generalis* (*C. generalis*) living body was collected from coastal area of Hainan Island and Xisha Islands. Small amount column centrifugal tissue/cell total RNA extraction kit (Shanghai Huashun Bioengineering Co., Ltd.) was used to extract total RNA according its operation manual, then cDNA synthesis was performed. Specific steps were carried out according to documents (e.g., QUAN Yaru, LUO Sulan, LIN Qiujin, ZHANGSUN Dongting, ZHANG Ben, Studying on extraction of conotoxin RNA and synthesis of cDNA thereof, Chinese Journal of Marine Drugs, 2005, 24(2): 1-5).

The above synthesized cDNA was used as template, a primer was designed according to untranslated region sequence of O1-gene superfamily precursor gene, and RT-PCR amplification was carried out to obtain specific PCR amplification product. The used primers were:

```
Primer 1:
                                 (SEQ ID NO: 13)
5'-CATCGTCAAGATGAAACTGACGTG-3';

Primer 2:
                                 (SEQ ID NO: 14)
5'-CACAGGTATGGATGACTCAGG-3'.
```

RT-PCR cycle program was: pre-denaturizing at 94° C. for 3 minutes, denaturizing at 94° C. for 30 seconds, annealing at 56° C. for 30 seconds, extending at 72° C. for 30 seconds, repeating for 30 cycles, then extending at 72° C. for 2 minutes.

The above specific PCR product was recovered, linked to T-easy vector (Promega) and used to transform *E. coli* XL1 strain (other commercial competent *E. coli* cells could also be used), recombinants were picked out using blue and white colonies and ampicillin resistance, recombinant plasmids were extracted and purified and used for sequencing, different clones (e.g., 3-5 different clones) of same one PCR product were used for sequencing and analysis.

Through sequence analysis and comparison, the cDNA gene of the O1-superfamily conotoxin new member, i.e., wild type propeptide GeXIVAWT, was obtained. The GeXIVAWT propeptide gene was analyzed with DNAStar software to obtain its open reading frame (ORF) sequence, i.e., SEQ ID NO: 1 and SEQ ID NO: 2, as follows:

Open reading frame (ORF) encoding GeXIVAWT proprotein (having allele mutation, the framed 19$^{th}$ T and G referred to single base mutation sites thereof; the underlined parts referred to DNA sequence encoding mature peptide):

(SEQ ID NO: 1)
ATGAAACTGACGTGCGTG[T]TGATCATCACCGTGCTGTTCCTGACGGCCTG

TCAACTCACTACAGCTGTGACTTACTCCAGAGGTGAGCATAAGCATCGTG

CTCTGATGTCAACTGGCACAAACTACAGGTTGCCCAAG<u>ACGTGCCGTAGT</u>

<u>TCCGGTCGTTATTGTCGCTCACCTTATGATTGCCGCAGAAGATATTGCAG</u>

<u>ACGCATTACGGATGCGTGCGTATAG</u>; or (SEQ ID NO: 2)
ATGAAACTGACGTGCGTG[G]TGATCATCACCGTGCTGTTCCTGACGGCCTG

TCAACTCACTACAGCTGTGACTTACTCCAGAGGTGAGCATAAGCATCGTG

CTCTGATGTCAACTGGCACAAACTACAGGTTGCCCAAG<u>ACGTGCCGTAGT</u>

<u>TCCGGTCGTTATTGTCGCTCACCTTATGATTGCCGCAGAAGATATTGCAG</u>

<u>ACGCATTACGGATGCGTGCGTATAG</u>

The new member of O1-superfamily conotoxin encoded with the above sequence, i.e., wild type propeptide GeXIVAWT (also called as αO-conotoxin GeXIVAWT precursor or αO-GeXIVAWT precursor or GeXIVAWT precursor hereinafter), had the following amino acid sequence (the framed 7$^{th}$ L and V referred to amino acids of mutation sites, the underlines parts referred to amino acid sequence of signal peptide, arrow ↓ referred to post-translational modification processing site before and after mature peptide, italic referred to N-terminal propeptide region):

(SEQ ID NO: 7)
<u>MKLTCV[L]IITVLFLTACQLTTA</u>*VTYSRGEHKHRALMSTGTNYRLPK*↓T

CRSSGRYCRSPYDCRRRYCRRITDACV; or (SEQ ID NO: 8)
<u>MKLTCV[V]IITVLFLTACQLTTA</u>*VTYSRGEHKHRALMSTGTNYRLPK*↓T

CRSSGRYCRSPYDCRRRYCRRITDACV.

The generated signal peptide and mature peptide encoded by precursor peptide cDNA gene of wild type GeXIVAWT were analyzed and predicted with online ProP 1.0 Server (Duckert, P.; Brunak, S.; Blom, N., Prediction of proprotein convertase cleavage sites. *Protein engineering, design & selection: PEDS* 2004, 17 (1), 107-12.).

The nucleotide sequence encoding GeXIVAWT mature peptide was as follows (the framed parts referred codons encoding cysteines):

(SEQ ID NO: 3)
ACC[TGC]CGTAGTTCCGGTCGTTAT[TGT]CGCTCACCTTATGAT[TGC]CGCAG

AAGATAT[TGC]AGACGCATTACGGATGC[TGC]GTATAG.

The amino acid sequence of GeXIVAWT wild type mature peptide (hereinafter also cited as αO-conotoxin GeXIVAWT or αO-GeXIVAWT or GeXIVAWT) was shown as follows (the framed parts referred to cysteines):

(SEQ ID NO: 9)
T[C]RSSGRY[C]RSPYD[C]RRRY[C]RRITDA[C]V.

The wild type GeXIVAWT precursor peptide contained 3 regions: signal peptide, propeptide and mature peptide, the 7$^{th}$ site amino acid residue in the signal peptide was leucine or valine (L or V), corresponding codons were TTG or GTG. The wild type mature peptide region (SEQ ID NO: 9) contained 5 cysteines (Cys), which was different from all known conotoxins, and the comparison with the related gene superfamily members was shown in Table 1.

TABLE 1

Comparison with conotoxin precursor protein sequences relating to αO-gene superfamily

| Super family | Name of peptide | Cysteine mode | Precursor peptide sequence |
|---|---|---|---|
| O$_1$ | αO-GeXIVA wild type | C-C-C-C-C | {MKLTCV(L/V)IITVLFLTACQLTTA}VTYSRGEHKHRALMSTGTNYRLPK ↓ TCRSSGRYCRSPYDC RRRYCRR ITDACV (SEQ ID NO: 15) |
| | αO-GeXIVA | C-C-C-C | {MKLTCV(L/V)IITVLFLTACQLTTA}VTYSRGEHKHRALMSTGTNYRLPK ↓ TCRSSGRYCRSPYDR RRRYCRR ITDACV (SEQ ID NO: 16) |
| | MVIIA | C-C-CC-C-C | {MKLTCVVIVAVLLLTACQLITA}DDSRGTQKHRALRSTTKLSTSTR↓[CKG KGAKCSRLMYDCCTGSCRSGKC]↓G (SEQ ID NO: 17) |
| O$_2$ | TxVIIA | C-C-CC-C-C | {MEKLTILLLVAAVLMSTQALI}QSDGEKRQQAKINFLS.RKS↓TAESWWE GECKGWSVYCSWDWECCSGECTRYYCELW (SEQ ID NO: 18) |
| O$_3$ | CaFr179 | C-C-CC-C-C | {MSGLGIMVLTLLLLVFMEA}SHQDAGEKQATQRDAINVRRRRSLARR↓[T VTEECEEDCEDEEKHCCNTNNGPSCARLCF]↓G (SEQ ID NO: 19) |

TABLE 1-continued

Comparison with conotoxin precursor protein
sequences relating to αO-gene superfamily

| Super family | Name of peptide | Cysteine mode | Precursor peptide sequence |
|---|---|---|---|
| J | PIXIVA | C-C-C-C | {MPSVRSVTCCCLLWMMFSVQLVTP}GSPGTAQLSGHRTAR↓]FPRPRIC NLACRAGIGHKYPFCHCR]↓GKRDAVSSSMAV (SEQ ID NO: 20) |
| L | LtXIVA | C-C-C-C | {MKLSVMFIVFLMLTMPMTCA}GISRSATNGGEADVRAHDKAANLMALLQ ER↓[MCPPLCKPSCTNC]↓G (SEQ ID NO: 21) |
| A | α-BuIA | CC-C-C | {MFTVFLLVVLTTTVVS}FPSDRASDGRNAAANDKASDVVTLVLK↓[GCCS TPPCAVLYC]↓GRRR (SEQ ID NO: 22) |
|  | αA-PIVA | CC-C-C-C-C | {MFTVFLLVVLATTVV}SFTSDRASDDRNTNDKASRLLSHVVR↓[GCCGS YPNAACHPCSCKDRPSYCGQ]↓GR (SEQ ID NO: 23) |
| C | αc-PrXA | C-C | {MQTAYWVMVMMMVMWITAPLSEG}GKPKLIIRGLVPNDLTPQRILRSLI SGR↓[TYGIYDAKPPFSCAGLRGGCVLPPNLRPKFKE]↓GR (SEQ ID NO: 24) |
| D | αD-VxXXA | C-CC-C-CC-C-C-C-C | {MPKLEMMLLVLLIFPLSYFIAAGG}QVVQVDRRGDGLAGYLQRGDR↓[D VQDCQVSTPGSKWGRCCLNRVCGPMCCPASHCYCVYHRGRGHGCSC] (SEQ ID NO: 25) |
| S | αS-RVIIIA | C-C-C-C-C-C-C-C-C | {MMSKMGAMFVLLLLFTLAS}SQQEGDVQARKTHPKREFQRILLRSGR↓ [KCNFDKCKGTGVYNCGESCSCEGLHSCRCTYNIGSMKSGCACICTYY] (SEQ ID NO: 26) |

In the above table, characters between braces represent signal peptide amino acids, italic characters represent N-terminal propeptide region amino acids, characters within square brackets represent mature peptide amino acids, arrows "↓" represent post-translational modification processing sites before and after a mature peptide; and characters within a parenthesis represent amino acids of a mutation site.

Example 2

Preparation and Sequence Analysis of New αO-Superfamily Conotoxin Gene Mutant Type (GeXIVA)

The 181$^{st}$ to 183$^{rd}$ bases TGC of the wild type GeX-IVAWT precursor peptide gene encoded cysteine (Cys), they were subjected to point mutation (could also be obtained by direct artificial chemical synthesis of SEQ ID NO: 4), that was, single base mutated and became a codon CGC (T GC→C GC) for coding arginine Arg (R), i.e., the 181$^{st}$ site T was changed into C (T181C), this point mutant was named as GeXIVA precursor peptide gene, and its sequence was as follows:

The open reading frame (ORF) (having allele mutation, the framed 19$^{th}$ T and G referred to its single base mutation site; the double underlined part referred to the 181$^{st}$ mutation site, and the underlined part referred to DNA sequence encoding mature peptide):

(SEQ ID NO: 4)

ATGAAACTGACGTGCGTGTTGATCATCACCGTGCTGTTCCTGACGGCCTG

TCAACTCACTACAGCTGTGACTTACTCCAGAGGTGAGCATAAGCATCGTG

CTCTGATGTCAACTGGCACAAACTACAGGTTGCCCAAGACGTGCCGTAGT

-continued

TCCGGTCGTTATTGTCGCTCACCTTATGATCGCCGCAGAAGATATTGCAG

ACGCATTACGGATGCGTGCGTATAG; or (SEQ ID NO: 5)

ATGAAACTGACGTGCGTGGTGATCATCACCGTGCTGTTCCTGACGGCCTG

TCAACTCACTACAGCTGTGACTTACTCCAGAGGTGAGCATAAGCATCGTG

CTCTGATGTCAACTGGCACAAACTACAGGTTGCCCAAGACGTGCCGTAGT

TCCGGTCGTTATTGTCGCTCACCTTATGATCGCCGCAGAAGATATTGCAG

ACGCATTACGGATGCGTGCGTATAG.

The above sequence coded new member of O1-superfamily conotoxin, i.e., mutant precursor peptide GeXIVA (hereinafter cited as αO-conotoxin GeXIVA precursor or αO-GeXIVA precursor or GeXIVA precursor) amino acid sequence (the framed 7$^{th}$ L and V referred to mutation site amino acid, the double underlined parts referred to the 61$^{st}$ site artificial mutation site, the underlined parts referred to the amino acid sequence of signal peptide, the arrow ↓ referred to post-translational modification processing site before and after mature peptide, italic referred to N-terminal propeptide region);

(SEQ ID NO: 10)

MKLTCVLIITVLFLTACQLTTA*VTYSRGEHKHRALMSTGTNYRLPK*↓T

CRSSGRYCRSPYDRRRRYCRRITDACV.

(SEQ ID NO: 11)

MKLTCVVIITVLFLTACQLTTA*VTYSRGEHKHRALMSTGTNYRLPK*↓T

CRSSGRYCRSPYDRRRRYCRRITDACV.

The generated signal peptide and mature peptide encoded by precursor peptide cDNA gene of mutant GeXIVA were analyzed and predicted with online ProP 1.0 Server (Duckert, P.; Brunak, S.; Blom, N., Prediction of proprotein convertase cleavage sites. *Protein engineering, design & selection: PEDS* 2004, 17 (1), 107-12.).

The nucleotide sequence encoding GeXIVA mature peptide was as follows (the framed parts referred codons encoding cysteines; the double underlined letter C referred to single base mutation site corresponding to point mutation amino acid):

(SEQ ID NO: 6)
ACG|TGC|CGTAGTTCCGGTCGTTAT|TGT|CGCTCACCTTATGAT|CGC|CGCAG
AAGATAT|TGC|AGACGCATTACGGATGCG|TGC|TATAG.

The amino acid sequence of GeXIVA mutant mature peptide (hereinafter also cited as αO-conotoxin GeXIVA or αO-GeXIVA or GeXIVA) was shown as follows (the framed parts referred to cysteines; the double underlined letter R referred to point mutation amino acid):

(SEQ ID NO: 12)
T|C|RSSGRY|C|RSPYD<u>R</u>RRRY|C|RRITDA|C|V.

The mutant GeXIVAWT precursor peptide contained 3 regions: signal peptide, propeptide and mature peptide, the 7$^{th}$ site amino acid residue in the signal peptide was leucine or valine (L or V), corresponding codons were TTG or GTG. The mutant mature peptide region (SEQ ID NO: 12) contained 4 cysteines (Cys), which was different from all known conotoxins, and the comparison with the related gene superfamily members was shown in the above Table 1.

The following studying shows that GeXIVA was a blocking agent for nAChRs and NMDARs, and had strongest blocking activity to α9α10 nAChR, so it was formally named as αO-conotoxin GeXIVA, aliased as αO-GeXIVA or GeXIVA.

Example 3

Artificial Synthesis of αO-Conotoxin GeXIVA

According to the amino acid sequence (SEQ ID NO: 12, C-terminal was not amidated) of αO-conotoxin GeXIVA mature peptide, the 3 possible isomer linear peptides GeXIVA12, GeXIVA13, GeXIVA14 (FIG. 1) of GeXIVA were artificially synthesized by Fmoc method. The specific method is as follows.

The resin peptides of the 3 isomers were artificially synthesized by Fmoc chemical method, in which except cysteines, residual amino acids were protected with standard side chain protecting groups. As for GeXIVA12, the —SH groups of its 3$^{rd}$ and 4$^{th}$ cysteines (Cys) were protected with Trt (S-trityl), and the —SH groups of its 1$^{st}$ and 2$^{nd}$ cysteines (Cys) were protected with Acm (S-acetamidomethyl) in pairs; as for GeXIVA13, the —SH groups of its 2$^{nd}$ and 4$^{th}$ cysteines (Cys) were protected with Trt (S-trityl), and the —SH groups of its 1$^{st}$ and 3$^{rd}$ cysteines (Cys) were protected with Acm (S-acetamidomethyl) in pairs; as for GeXIVA14, the —SH groups of its 2$^{nd}$ and 3$^{rd}$ cysteines (Cys) were protected with Trt (S-trityl), and the —SH groups of its 1$^{st}$ and 4$^{th}$ cysteines (Cys) were protected with Acm (S-acetamidomethyl) in pairs. The synthesis steps comprise: using Fmoc and FastMoc methods of solid phase synthesis method, synthesizing 3 isomer linear peptides by ABI Prism 433a polypeptide synthesizer. The side chain protecting groups of Fmoc amino acids were: Pmc (Arg), Trt (Cys), But (Thr, Ser, Tyr), OBut (Asp), Boc (Lys). Fmoc HOBT DCC method was used, and its steps were carried out according to synthesis manual of instrument. In order to complete synthesis, piperidine deprotecting time and coupling time were properly extended, respectively, double coupling was used for amino acids difficult to link, and thus the resin peptides were obtained. The linear peptide was cut from resin using reagent K (trifluoroacetic acid/water/ethanedithiol/phenol/thioanisole; 90:5:2.5:7.5:5,v/v/v/v/v), and subjected to ice diethyl ether precipitation and washing to recover a crude product of the linear peptide, preparative reversed phase HPLC C18 column (Vydac) was used for purification, and elution linear gradient was 10-50% B60 within 0-40 min. Solution B was 60% ACN (acetonitrile), 40% H20, 0.92% TFA (trifluoroacetic acid); solution A was 1% TFA aqueous solution.

The purified linear peptide was subjected to purity detection with HPLC C18 column (Vydac), showing its purity was 96% or more, then it could be used for oxidation folding. The linear peptides of 3 isomers, GeXIVA12, GeXIVA13 and GeXIVA14, were subjected to two-step oxidation folding reaction according to documents (Dowell, C.; Olivera, B. M.; Garrett, J. E.; Staheli, S. T.; Watkins, M.; Kuryatov, A.; Yoshikami, D.; Lindstrom, J. M.; McIntosh, J. M., Alpha-conotoxin PIA is selective for alpha6 subunit-containing nicotinic acetylcholine receptors. *The Journal of neuroscience* 2003, 23 (24), 8445-52.), and the process thereof was briefly described as follows:

Firstly, the first pair of disulfide bond between two cysteines with Trt protecting groups was formed by potassium ferricyanide method (20 mM potassium ferricyanide, 0.1 M Tris, pH 7.5, 30 min). After monocycle peptide was purified with reversed phase HPLC C18 column (Vydac), iodine oxidation was carried out (10 mM iodine in H$_2$O:trifluoroacetic acid:acetonitrile (78:2:20 by volume, 10 min), to remove Acm of another 2 cysteines, and form the second pair of disulfide bond between the 2 cysteines at the same time. Dicyclic peptide was purified with reversed phase HPLC C18 column (Vydac) to obtain αO-conotoxin in which disulfide bonds were directionally formed between corresponding cysteines in sequence of N-terminal to C-terminal, and confirmed with mass spectrum (MS). The theoretical molecular weight (monoisotopic mass) of the 3 isomers after oxidation folding was 3451.96 Da, the measured molecular weight of GeXIVA12 was 3451.83 Da; the measured molecular weight of GeXIVA13 was 3451.72 Da; and the measured molecular weight of GeXIVA14 was 3452.05 Da. Colorimetric assay was used to detect polypeptide concentration under wavelength of 280 nm, and polypeptide concentration and mass were calculated according to Beer-Lambert (equation). These quantified isomers were continuously used for subsequent activity assay (e.g., Example 5-10).

Example 4

Expression of Rat, Mice and Human nAChRs Subtypes in *Xenopus* Oocytes

The method of document (Azam L, Yoshikami D, McIntosh J M. Amino acid residues that confer high selectivity of the alpha6 nicotinic acetylcholine receptor subunit to alpha-conotoxin MII[S4A,E11A,L15A]. J Biol Chem. 2008; 283 (17):11625-32.), the specification of in vitro transcription kit (mMessage mMachine in vitro transcription kit (Ambion, Austin, Tex.)) were referred to prepare various rat nervous type nAChRs subtypes (α3β2, α6/α3β2β3, α6/α3β4, α9α10, α4β2, α4β4, α3β4, α2β2, α2β4, α7), human nervous type nAChRs subtypes (α9α10, α6/α3β2β3, α7), various mutants of rat α9α10 nAChR, and cRNA of mice and human muscle type nAChRs (α1β1δε), their concentrations were measured and calculated by OD values under UV 260 nm. The oocytes (frogspawns) of *Xenopus* (*Xenopus laveis*) were collected and dissected, cRNA was injected into frogspawns, the injection dose for each subtype was 5 ng cRNA. For muscle nAChR, each subtype was injected with 0.5-2.5 ng DNA. The frogspawns were cultured in ND-96. The collected frogspawns were injected with cRNA within 1-2 days, and used for nAChRs voltage clamp recording within 1-4 days after the injection. $Ba^{2+}$-contained ND-96 buffer solution was obtained by replacing $CaCl_2$ with $BaCl_2$ at equivalent molar concentration. The prepared samples were used for example in following Examples 5-10.

Example 5

Experiment of Blocking Various Rat nAChRs with 3 Isomers of αO-Conotoxin GeXIVA

One of frogspawns injected with cRNA was placed in 30 uL of Sylgard record tank (diameter 4 mm×depth 2 mm), gravity perfused with ND96 perfusate (96.0 mM NaCl, 2.0 mM KCl, 1.8 mM $CaCl_2$, 1.0 mM $MgCl_2$, 5 mM HEPES, pH 7.1-7.5) containing 0.1 mg/ml BSA (bovine serum albumin), or ND96 (ND96A) containing 1 mM atropine, flow rate was 1 ml/min. All conotoxin solutions also contained 0.1 mg/ml BSA to reduce non-specific adsorption of toxin, a change-over valve (SmartValve, Cavro Scientific Instruments, Sunnyvale, Calif.) could be used for freely switching between perfusion of toxin and acetylcholine (ACh), and a series of three-way solenoid valves (solenoid valves, model 161TO31, Neptune Research, Northboro, Mass.) were used for freely switching between perfusion of ND96 and ACh. Ach gating current was set at "slow" clamp with double-electrode voltage clamp amplifier (model OC-725B, Warner Instrument Corp., Hamden, Conn.), and on-line recording of clamp gain was performed at the maximum value (×2000) position. Glass electrodes were drawn from glass capillaries (fiber-filled borosilicate capillaries, WPI Inc., Sarasota, Fla.) with 1 mm external diameter×0.75 mm internal diameter, and filled with 3 M KCl as voltage and current electrodes. Membrane voltage was clamped at −70 mV. The control of whole system and data recording were carried out with a computer. ACh pulse was automatically perfusing ACh for 1 s per interval of 5 min. ACh had concentration of 10 μM for oocytes of muscle type nAChRs and nervous type α9α10 nAChRs; 200 μM for α7 of nervous type nAChRs, and 100 μM for other subtypes. At least 4 oocytes were used for recording situations of current response and current track of a subtype under different toxin concentrations.

The measured current data were subjected to statistic analysis with GraphPad Prism software (San Diego, Calif.), dose-response curves were plotted, half-blocking concentration ($IC_{50}$) of conotoxin and many other parameters relating to toxin-blocking nAChRs were calculated.

The results shown that 33 nM αO-GeXIVA12 (prepared in Example 3) completely blocked the current generated by Ach-gated α9α10 nAChR open, and had features of fast elution and reversible blocking (FIG. 2A). All of 3 isomers had strong blocking activity to α9α10 nAChR. Among the 3 isomers, αO-GeXIVA12 had the strongest activity, αO-GeXIVA14 took the second place, and αO-GeXIVA13 had the weakest activity (FIG. 2 B, C, D). Their half-blocking doses ($IC_{50}$) and error ranges separately were: GeXIVA12, 4.6 nM (3.18-6.65 nM); GeXIVA13, 22.7 nM (11.8-43.5 nM); GeXIVA14, 7 nM (3.6-13.4 nM). The dose-response curves of the 3 isomers separately had slopes (Hillslope) and error ranges as follows: GeXIVA12, 0.56 (0.44-0.69); GeXIVA13, 0.78(0.29-1.26), GeXIVA14, 0.79 (0.23-1.36). The αO-GeXIVA12 had different blocking activity on various nAChRs subtypes, and its half-blocking doses $IC_{50}$ and slopes of dose-response curves were shown in Table 2.

TABLE 2

Half-blocking doses $IC_{50}$ and slopes of dose-response curves of αO-GeXIVA12 to various nAChRs subtypes

| nAChRs subtype | Half-blocking dose $IC_{50}$ (nM)[a] | Ratio to half-blocking dose of α9α10 subtype[b] | Slope of dose-response curve[3] |
|---|---|---|---|
| α9α10 | 4.61 (3.18-6.65) | 1 | 0.56 (0.44-0.69) |
| α7 | 415 (264-655) | 90.0 | 1.12 (0.68-1.56) |
| Mouse α1β1δε | 394 (311-498) | 85.5 | 1.71 (0.98-2.43) |
| α6/α3β2β3 | 258 (200-331) | 56.0 | 0.63 (0.53-0.72) |
| α6/α3β4 | 806 (453-1140) | 175.2 | 1.18 (0.57-1.79) |
| α2β2 | 338 (178-640) | 73.3 | 1.133 (0.33-1.94) |
| α2β4 | 2090 (1430-3070) | 454.3 | 1.12 (0.73-1.51) |
| α3β2 | 412 (223-761) | 89.6 | 1.033 (0.37-1.70) |
| α3β4 | 5400 (3390- to 8580) | 1171 | 1.12 (0.47-1.77) |
| α4β2 | 979 (672-1425) | 212.4 | 0.083 (0.51-0.86) |
| α4β4 | 2390 (1560-3670) | 662.9 | 0.21 (0.67-1.65) |

Figure 3:
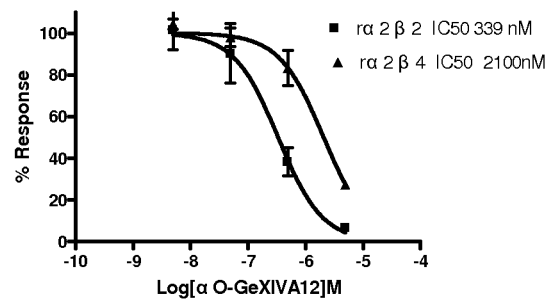
FIG. 3: shows concentration dose-response curves (A-E) of αO-GeXIVA12 to other nAChRs subtypes. In the figure, abscissa is log value (Log [Toxin Concentration]M) of molar concentration (M) of the used αO-GeXIVA12; ordinate is dose-response percentage (% Response), which is a ratio percentage of acetylcholine receptor current to control current under action of toxin of corresponding concentration, each dose-response percentage is a mean value (mean) of data of 6-12 *Xenopus* oocytes, and the curve shows standard error (SEM) at the same time. The figure indicates corresponding nAChRs subtype and half-blocking dose ($IC_{50}$) for the subtype. The αO-GeXIVA12 shows diverse activity in blocking α*β4 and α*β2 nAChRs, has activity of blocking α*β2 nAChRs considerably higher than that of α*β4 nAChRs; and has similar activity in blocking mice muscle type nAChR (Mα1β1δε) and α7 nAChR subtypes.
Figure 3:
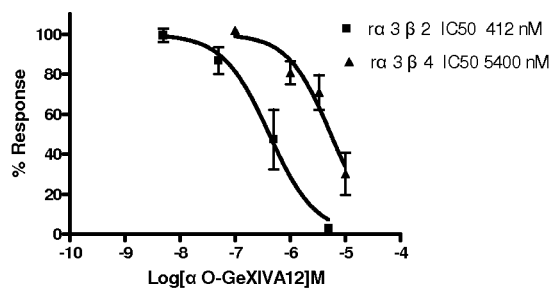
Figure 3:
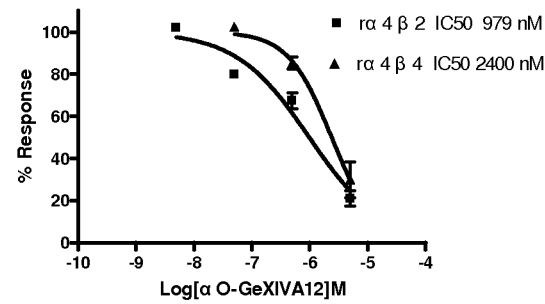
Figure 3:
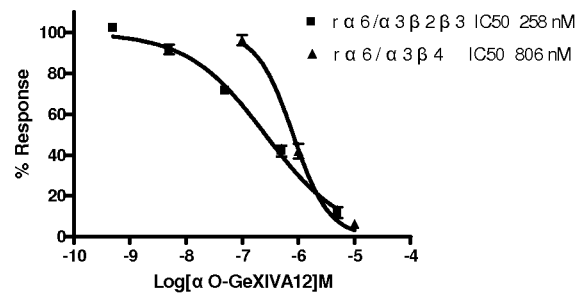
Figure 3:
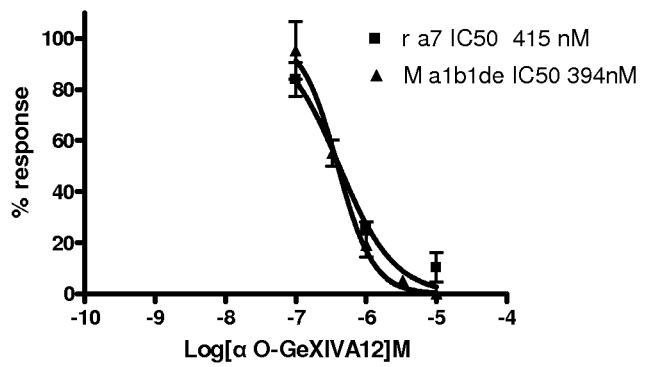

Notation:
[a] value in bracket had confidence interval of 95%;
[b] referred to nAChR subtype $IC_{50}$ /α9α10 $IC_{50}$;

The difference of blocking activity of αO-GeXIVA12 to α*β4 and α*β2 nAChRs was relatively great, the blocking activity to α*β2 nAChRs was far greater than that to α*β4 nAChRs (FIG. 3, A-E); the blocking activity to mice muscle type nAChR (Mα1β1βε) and to α7 nAChR subtype were relatively close. It was shown that αO-GeXIVA12 more preferably blocked β2-containing nAChRs, including α6/α3β2β3, α4β2, α3 β2 and α2β2. The blocking activity of αO-GeXIVA12 to α9α10 nAChR was at least 56-663 times higher than that to other subtypes. Under a low concentration of less than 200 nM, αO-GeXIVA12 was a specific blocking agent for α9α10 nAChR, but had very weak or almost not blocking activity to other nAChRs subtypes. The comparison of action target biological activity of αO-GeXIVA12 and other superfamily conotoxins was shown in Table 3.

TABLE 3

Comparison of properties between αO-GeXIVA and other conotoxins

| Name of toxin peptide | Kind of source | Sequence | Target | Molecular weight |
|---|---|---|---|---|
| αO-GeXIVA | C. generalis | TCRSSGRYCRSPYDRRRRYC RRITDACV^ | α9α10 nAChR >> α*β2 nAChRs >> α*β4 nAChRs nAChRs > NMDAR | 3452 |
| ω-MVIIA | C. magus | CKGKGAKCSRLMYDCCTGSC RSGKC# | Cav2.2 > Cav2.1 N > P/Q | 2637 |
| pI14a (κJ-PIXIVA) pI14a (αJ-PIXIVA) | C. planorbis | FPRPRICNLACRAGIGHKYPF CHCR# | Kv1.6 > 1.1 > 1.2~1.3~1.4~1.5~2.1~3.4 Muscle > α3β2 nAChRs | 2909 |
| lt14a (αL-LtXIVA) | C. litteratus | MCPPLCKPSCTNC# | Neuronal nAChR | 1391 |
| vil14a (KL-VilXIVA) | C. Villepinii | GGLGRCIYNCMNSGGGLSFIQ CKTMCY^ | N.D. | 2871 |
| ψ-PIIIE | C. purpurascens | HOOCCLYGKCRRYOGCSSAS CCQR# | Muscle nAChR | 2715 |
| α-LtIA | C. litteratus | GCCARAACAGIHQELC# | α3β2 > α6/α3β2β3 | 1600 |
| αA-EIVA | C. ermineus | GCCGPYONAACHOCGCKVG ROOYCDROSGG# | Muscle nAChR | 3094 |
| αC-PrXA | C. parius | TYGIYDAKPOFSCAGLRGGCV LPONLROKFKE# | Muscle nAChR | 3539 |
| αD-VxXXB | C. vexillum | DDγSγCIINTRDSPWGRCCRT RMCGSMCCPRNGCTCVYHW RGHGCSCPG (dimer) | α7 > α3β2 | 5735 |
| αS-RVIIIA | C. radiatus | KCNFDKCKGTGVYNCG(Gla)S CSC(Gla)GLHSCRCTYNIGSM KSGCACICTYY | Muscle nAChR Neuronal nAChR | 5167 |

Figure 4:
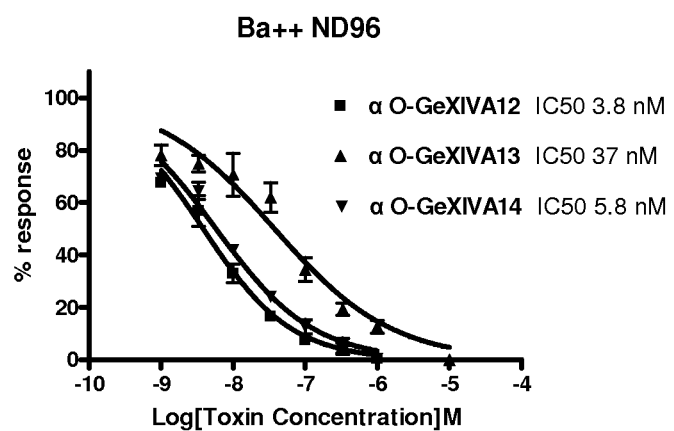
FIG. 4: shows concentration dose-response curves of 3 isomers, αO-GeXIVA12, GeXIVA13 and GeXIVA14, to α9α10 nAChR when conventional ND96 perfusate is replaced with barium ion DN96 perfusate ($Ba^{++}$-ND96), in which abscissa refers to log value (Log [Toxin Concentration]M) of molar concentration (M) of the used 3 αO-GeXIVA isomers; ordinate is dose-response percentage (% Response), which is a ratio percentage of acetylcholine receptor current to control current under action of toxin of corresponding concentration, each dose-response percentage is a mean value (mean) of data of 9 *Xenopus* oocytes, and the curve shows standard error (SEM) at the same time. The figure also indicates half-blocking dose ($IC_{50}$) of corresponding isomer to α9α10 nAChR subtype.

It was known that α9α10 nAChR has very high permeability to calcium ion ($Ca^{++}$). The calcium ion internal flow of nAChRs could activated the generation of chlorine ion ($Cl^-$) external flow, at for xenopus oocytes, this kind of current was 90% or more of the observed α9α10nAChR open current. On the contrary, barium ion ($Ba^{++}$) that was close to calcium ion did not activate chlorine ion current. Thus, we used barium ion ND96 perfusate ($Ba^{++}$-ND96, 1.8 mM $BaCl_2$ replaced $CaCl_2$) to replace conventional ND96 perfusate, and found that the observed open current of α9α10nAChR was far lower than that of the conventional ND96 perfusate, which was consistent with the previous studying. Under condition of barium ion ND96 perfusate, GeXIVA12 showed the strongest blocking activity to α9α10nAChR, GeXIVA14 took the second place, and the activity of GeXIVA13 was the weakest (FIG. 4). As for the isomer αO-GeXIVA12 having I-II and III-IV disulfide bonds, its half-blocking dose ($IC_{50}$) to α9α10 nAChR and error range thereof were 3.8 nM (3.1-4.8 nM), curve slope (Hillslope, nH) and error range thereof were 0.71 (0.58-0.84); as for the isomer αO-GeXIVA13 having I-III and II-IV disulfide bonds, its half-blocking dose ($IC_{50}$) to α9α10 nAChR and error range thereof were 37 nM (25.0-55.7 nM), curve slope (Hillslope) and error range thereof were 0.54 (0.42-0.65); as for the isomer αO-GeXIVA14 having I-IV and II-III disulfide bonds, its half-blocking dose ($IC_{50}$) to α9α10 nAChR and error range thereof were 5.8 nM (4.7-7.1 nM), curve slope (Hillslope) and error range thereof were 0.65 (0.56-0.73). Under condition of barium ion ND96 perfusate, the 3 isomers of αO-GeXIVA had results of activity similar to those under calcium ion-containing normal ND96 perfusate. In addition, under barium ion-ND96, the activities of αO-GeXIVA12 and αO-GeXIVA14 were stronger than those under calcium ion-containing normal ND96, while the activity of αO-GeXIVA13 under barium ion-ND96 was stronger than that under normal ND96. Thus, the 3 isomers of GeXIVA did block α9α10nAChR, instead of blocking chlorine ion current that was activated due to calcium ion.

Example 6

Experiment of 3 Isomers of αO-Conotoxin GeXIVA Blocking Rat NMDA Receptor

Figure 5:
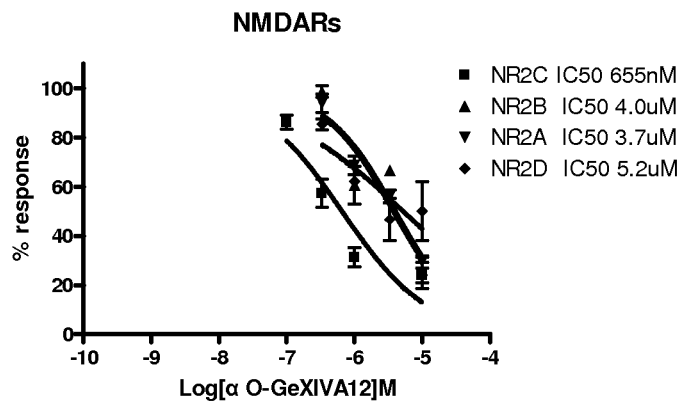
FIG. 5: shows concentration dose-response curves of αO-GeXIVA12 to various NMDA receptor subtypes, in which abscissa refers to log value of molar concentration (M) of the used αO-GeXIVA12; ordinate is dose-response percentage (% Response), which is a ratio percentage of NMDA receptor current to control current under action of toxin of corresponding concentration, each dose-response percentage is a mean value (mean) of data of 3-5 *Xenopus* oocytes, and the curve shows standard error (SEM) of 95% confidence interval at the same time. The figure also indicates half-blocking dose ($IC_{50}$) of corresponding NMDARs subtype to said subtype.

The method of document (Twede, V. D. et al. Conantokin-Br from Conus brettinghami and selectivity determinants for the NR2D subunit of the NMDA receptor. Biochemistry, 2009, 48: 4063-4073) was referred to, and method similar to expression of nAChRs in xenopus oocytes was used to prepare cRNAs corresponding to 4 subtypes of rat NMDA receptor: NR1-2b/NR2A, NR1-2b/NR2B, NR1-2b/NR2C, NR1-2b/NR2D, which concentrations were measured and calculated with OD values under UV 260 nm. The oocytes (frogspawns) of Xenopus (Xenopus laveis) were collected and dissected, cRNA was injected into frogspawns, the injection dose for each subtype was 5 ng cRNA. The frogspawns were cultured in ND-96. The collected frogspawns were injected with cRNA within 1-2 days, and used for nAChRs voltage clamp recording within 1-4 days after the injection. Voltage clamp recording NMDA receptor current was carried out by a method similar to that of nAChRs, except that the used perfusate was magnesium-free ND96 perfusate ($Mg^{2+}$-free ND96 buffer), which composition comprised 96.0 mM NaCl, 2.0 mM KCl, 1.8 mM CaCl2, 5 mMHEPES (pH 7.2-7.5). The reason was that $Mg^{2+}$ could block NMDA receptor under −70 mV clam voltage. The NMDA receptor agonist solution was $Mg^{2+}$-free ND96 that contained 200 μM glutamate and 20 μM glycine in final concentration. The αO-GeXIVA12 had the strongest blocking activity to NR2C NMDAR subtype, and can be rapidly eluted. As for αO-GeXIVA12, its half-blocking doses ($IC_{50}$) and error range thereof to 4 kinds of NMDA receptor subtypes separately were: NR2C, 0.66 μM (0.38-1.1 μM); NR2B, 4.0 μM (2.2-7.3 μM); NR2A, 3.7 μM (2.8-5.0 μM); NR2D, 5.2 μM (1.7-15.7 μM); as for αO-GeXIVA12, its dose-response curve slopes (Hillslope) and error ranges thereof to 4 kinds of NMDA receptor subtypes separately were: NR2C, 0.13 (0.42-0.97); NR2B, 0.22(0.36-1.3); NR2A, 0.10 (0.61-1.07); NR2D, 0.15 (0.10-0.78) (FIG. 5). The half-blocking doses ($IC_{50}$) and dose-response curve slopes of 3 isomers of αO-GeXIVA to subtypes of various NMDARs were shown in Table 4.

the order of their $IC_{50}$ activities was αO-GeXIVA12, 415 nM>αO-GeXIVA14, 1740 nM>αO-GeXIVA13, 4960 nM. The activity order of αO-GeXIVA12>GeXIVA14>GeXIVA13 also occurred in mice muscle type nAChR and nervous type α3β2 nAChR, but the diversity of blocking activities between the 3 isomers to Mα1β1δε and α3β2 nAChRs was very small.

As for the blocking activities to α2β2, α2β4, α4β2, α4β4 nAChRs, the blocking activity of GeXIVA14 was the strongest, the $IC_{50}$ to α2β2 was merely 122 nM, the $IC_{50}$ to α4β2 was 200 nM. As for the blocking activities to α3β4, α6/α3β4 nAChR, the blocking activity of GeXIVA13 was the strongest, which $IC_{50}$ was 483 nM; GeXIVA14 took the second place, which $IC_{50}$ was 611 nM; while GeXIVA12 showed the weakest blocking activity, which $IC_{50}$ was 806 nM. However, the blocking activities of the 3 isomers to all other nAChRs subtypes were far less than that to α9α10 nAChR. The differential blocking activities of the 3 isomers to different nAChRs subtypes provided a theoretical basis for designing a series of selective blocking agents using GeXIVA as template for different subtypes.

TABLE 4

Half-blocking doses ($IC_{50}$) and dose-response curve slopes of 3 isomers of αO-GeXIVA to subtypes of various NMDARs

| Isomer | NMDARs subtype | NR2A | NR2B | NR2C | NR2D |
|---|---|---|---|---|---|
| GeXIVA12 | $IC_{50}$ (nM)[a] | 3700 (2800-5000) | 4000 (2200-7300) | 655 (380-1100) | 5200 (1700-15700) |
| | slope | 0.84 (0.61-1.07) | 0.85 (0.36-1.33) | 0.69 (0.42-0.97) | 0.44 (0.10-0.78) |
| GeXIVA13 | $IC_{50}$ (nM) | >10000 | >10000 (17000) | ≥10000 | ≥10000 |
| | slope | — | — | — | — |
| GeXIVA14 | $IC_{50}$ (nM) | 7400 (3800-14000) | 3400 (1500-7700) | >10000 | ≥10000 |
| | slope | 1.08 (0.15-2.01) | 0.94 (0.28-1.60) | — | — |

Notation:
[a]value in bracket had confidence interval of 95%.

The activities of αO-GeXIVA12 to 4 kinds of NMDA receptor subtypes were in sequence from strong to weak as follows: NR2C>NR2A>NR2B>NR2D. The αO-GeXIVA14 had relatively weak blocking activity to 2 kinds of NMDA receptor subtypes NR2B and NR2A, while αO-GeXIVA13 had very weak or even no blocking activity to 4 kinds of NMDA receptor subtypes.

Example 7

Figure 6:
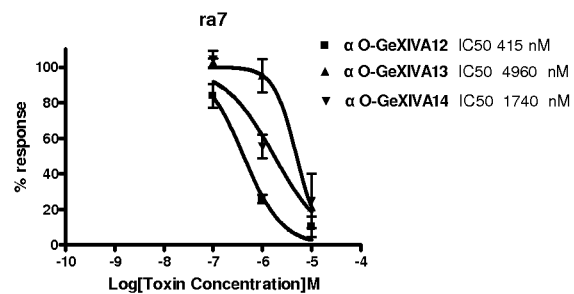
FIG. 6: shows concentration dose-response curves (A-J) of 3 isomers, αO-GeXIVA12, αO-GeXIVA13 and αO-GeXIVA14, to various other subtypes of nAChR receptor, in which the signs have the same meanings of FIG. 3
Figure 6:
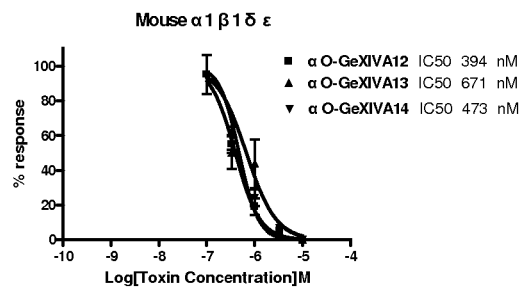
Figure 6:
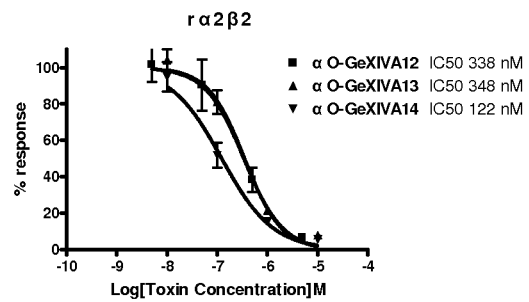
Figure 6:
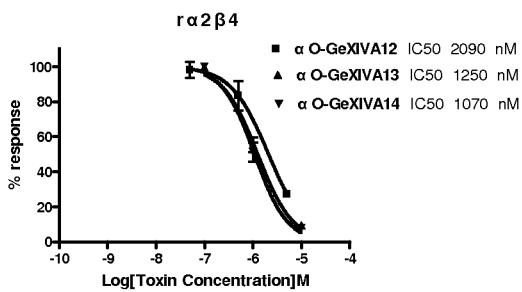
Figure 6:
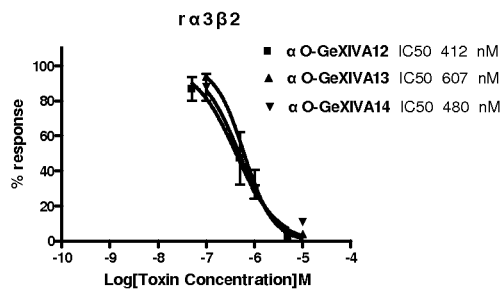
Figure 6:
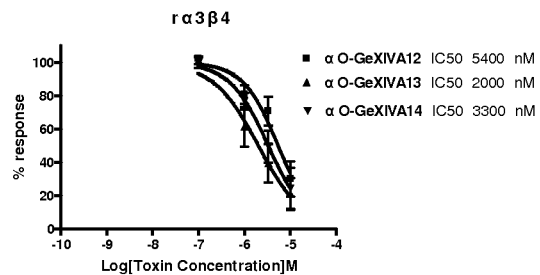
Figure 6:
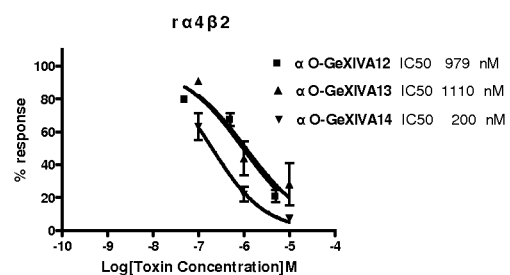
Figure 6:
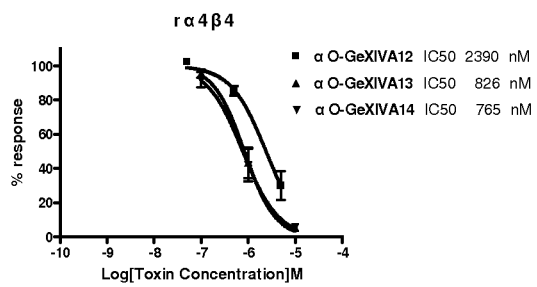
Figure 6:
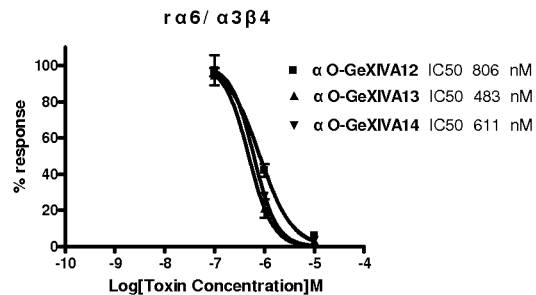
Figure 6:
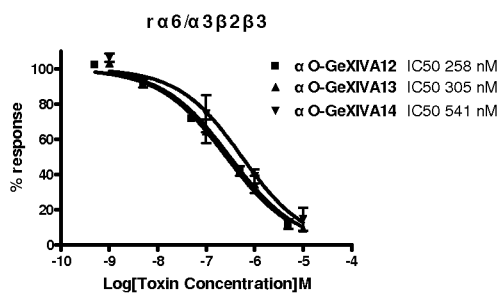

Experiments of 3 Isomers of αO-Conotoxin GeXIVA Blocking Other Rat nAChRs and Mice Muscle Type nAChRs The same experimental methods of Examples 4 and 5 were used to study the effects of 3 isomers of αO-conotoxin GeXIVA on blocking other rat nAChRs and mice muscle type nAChRs. The concentration dose-response curves of 3 isomers, αO-GeXIVA12, αO-GeXIVA13 and αO-GeXIVA14, to other subtypes of nAChR receptors were shown in FIG. 6 (A-J). Generally, the blocking activates of the 3 isomers to α*β2 nAChRs were higher that those to α*β4 nAChRs (FIG. 6); the blocking activities of 3 isomers to mice muscle type nAChR (Mα1β1δε) were similar, and their half-blocking doses ($IC_{50}$) separately were: αO-GeXIVA12, 394 nM; αO-GeXIVA13, 671 nM; αO-GeXIVA14, 473 nM. However, the blocking activities of the 3 isomers to α7 nAChR subtype were greatly diverse, Example 8

Experiment of 3 Isomers of αO-Conotoxin GeXIVA Blocking Human nAChRs

Figure 7:
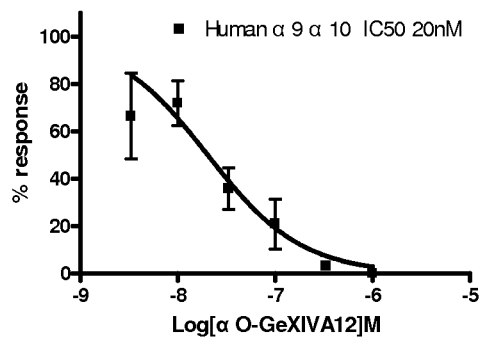
FIG. 7: shows concentration dose-response curves (A-F) of 3 isomers, αO-GeXIVA12, αO-GeXIVA13 and αO-GeXIVA14, to human nAChR receptor associated subtypes, in which the signs have the same meanings of FIG. 3.
Figure 7:
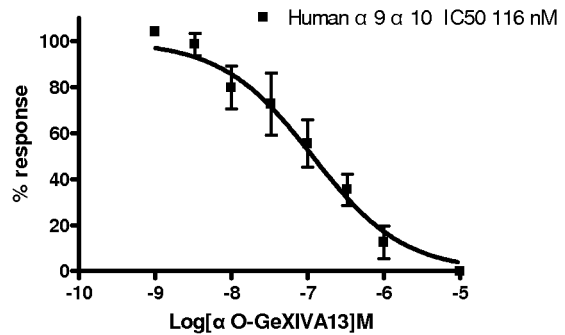
Figure 7:
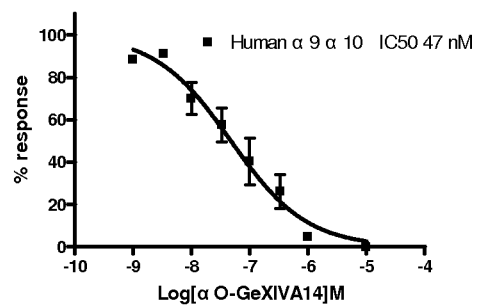
Figure 7:
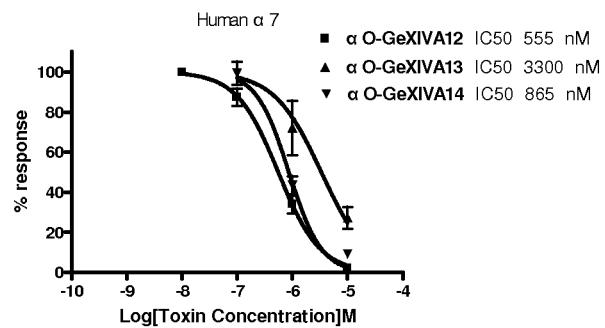
Figure 7:
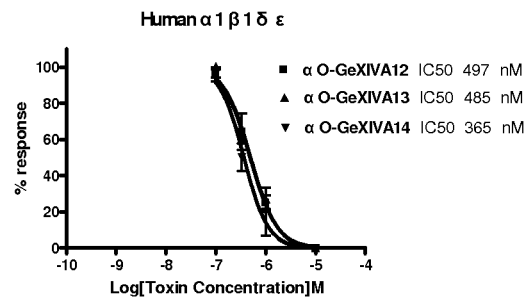
Figure 7:
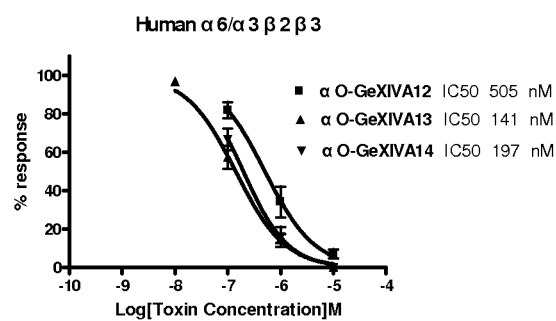

The same experimental methods of Examples 4 and 5 were used to study the effects of 3 isomers of αO-conotoxin GeXIVA on blocking human nAChRs. Among the 3 isomers, both αO-GeXIVA12 and GeXIVA14 showed very strong blocking activities to human α9α10 nAChR, αO-GeXIVA12 had the strongest activity, αO-GeXIVA14 took the second place, and αO-GeXIVA13 showed the weakest activity (FIG. 7, A-F). Their half-blocking doses ($IC_{50}$) and error range thereof separately were: GeXIVA12, 20 nM (12.4-33.2 nM); GeXIVA13, 116 nM (65.4-204 nM); GeXIVA14, 47 nM (29.7-75.3 nM). The slopes of dose-response curves (Hillslope) of the 3 isomers and error ranges thereof separately were: GeXIVA12, 0.91(0.49-1.32); GeXIVA13, 0.73(0.45-1.01), GeXIVA14, 0.67(0.46-0.88). The blocking activities of the 3 isomers to human muscle type nAChR (Human α1β1δε) were similar, and their half-blocking doses ($IC_{50}$) separately were: αO-GeXIVA12, 497 nM; αO-GeXIVA13, 485 nM; αO-GeXIVA14, 365 nM. However, the blocking activities of the 3 isomers to α7 nAChR subtype were very diverse, and their $IC_{50}$ activity order was αO-GeXIVA12, 555 nM>αO-GeXIVA14, 865 nM>αO-GeXIVA13, 3300 nM. The blocking activity order to human α9α10 and α7 nAChRs, αO-GeXIVA12>GeXIVA14>GeXIVA13, was consistent to the blocking activity order to mice α9α10 and α7 nAChRs. However, the blocking activity order of the 3 isomers to human α6/α3β2β3 nAChR was αO-GeXIVA13≥GeXIVA14>GeXIVA12, and their half-blocking doses (IC$_{50}$) separately were: αO-GeXIVA13, 141 nM; αO-GeXIVA14, 197 nM; αO-GeXIVA12, 505 nM. The differential blocking activities of the 3 isomers to different human nAChRs subtypes were advantageous to design a series of αO-GeXIVA analogues so as to obtain selective blocking agents for different subtypes.

Example 9

Figure 8:
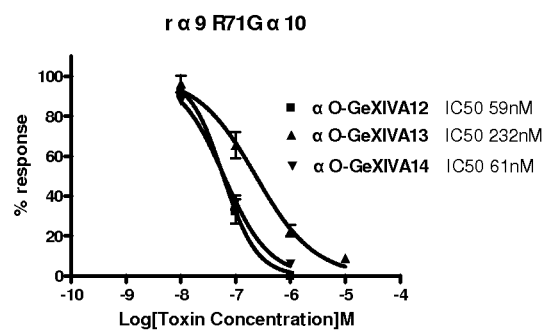
FIG. 8: shows concentration dose-response curves (A-K) of 3 isomers, αO-GeXIVA12, αO-GeXIVA13 and αO-GeXIVA14, to various mutant types of rat α9α10 nAChR receptor, in which the signs have the same meanings of FIG. 3.
Figure 8:
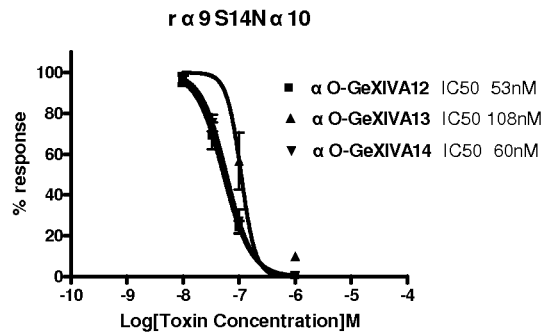
Figure 8:
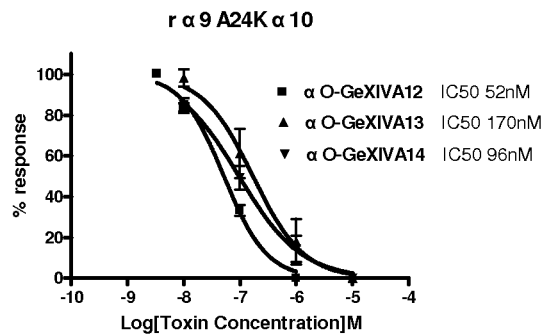
Figure 8:
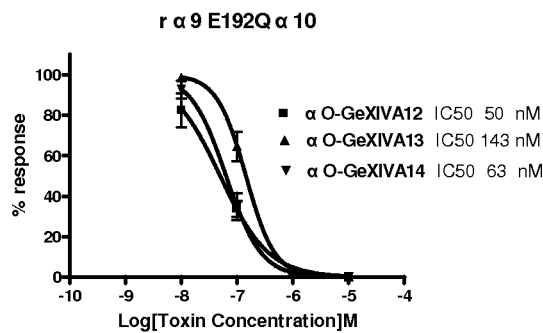
Figure 8:
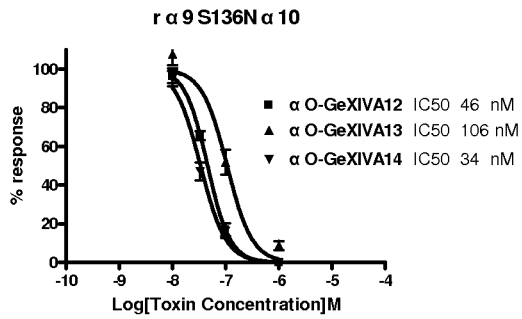
Figure 8:
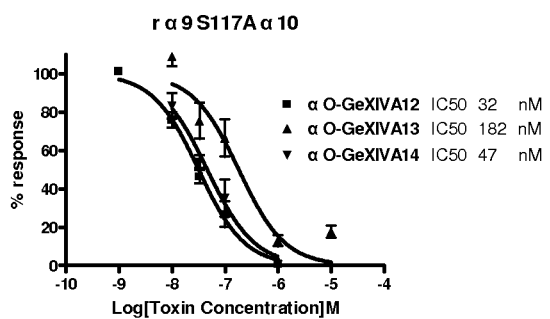
Figure 8:
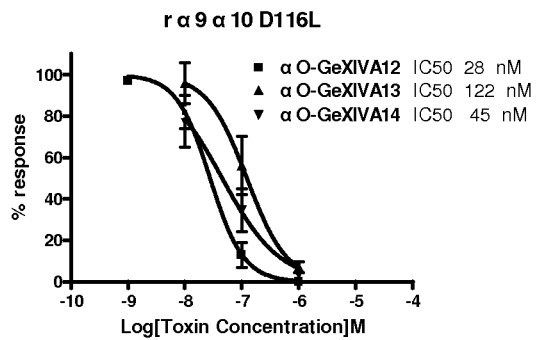
Figure 8:
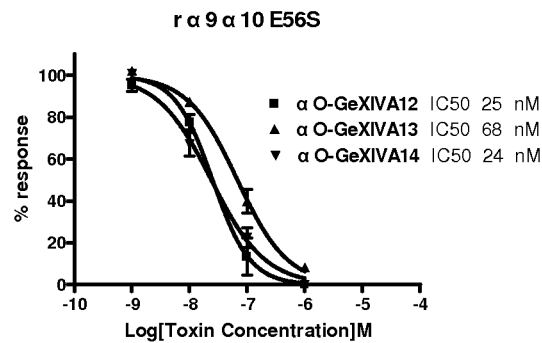
Figure 8:
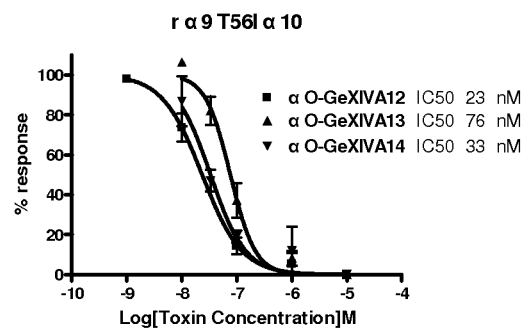
Figure 8:
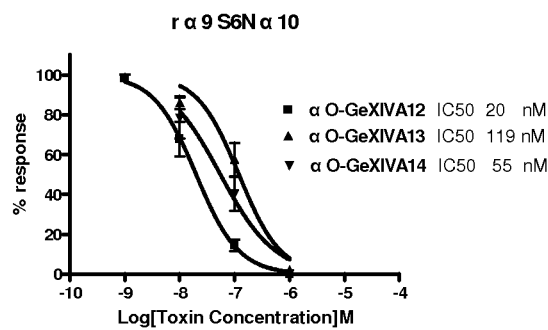
Figure 8:
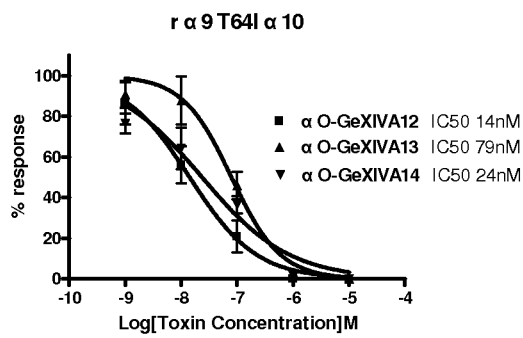

Experiment of 3 Isomers of αO-Conotoxin GeXIVA Blocking Various Mutants of Rat α9α10 nAChR Receptor The possible key amino acids of wild type α9α10 nAChR receptor at sites binding to conotoxin were subjected to point mutation, i.e., change of single amino acid, to prepare various mutants of α9α10 nAChR receptor. The mutation sites were shown in FIG. 8, for example, "rα9R71Gα10" referred to that in α9 subtype of rat (r) wild type α9α10 nAChR receptor, the 71$^{st}$ arginine R(Arg) was mutated into glycine G(Gly), and the representing methods of other mutants were in the same manner. The receptor mutants were prepared by PCR method, i.e., subjecting the codons corresponding to point mutation amino acids in gene of α9 or α10 subtype of wild type α9α10 nAChR receptor to mutation. As for the obtained mutants, the effects of 3 isomers of αO-conotoxin GeXIVA on blocking various α9α10 nAChRs mutants were studied according to the same experimental methods of Examples 4 and 5 (FIG. 8).

The blocking activities of the 3 isomers, αO-GeXIVA12, αO-GeXIVA13 and αO-GeXIVA14, to 11 rat α9α10 nAChR receptor mutants were tested. Their concentration dose-response curves were shown in FIG. 8 (A-K). The general trend was that all of the 3 isomers had very strong blocking activity to various mutants of α9α10 nAChR, the blocking activities of αO-GeXIVA12 and αO-GeXIVA14 to various mutants were similar, and stronger than the activity of αO-GeXIVA13, which was in consistence with the blocking activity order of the wild type α9α10 nAChR. The blocking activity order of the 3 isomers was αO-GeXIVA12≥GeXIVA14>GeXIVA13. There were 5 mutants having relatively great change of activity, the half-blocking dose IC$_{50}$ of αO-GeXIVA12 was 46-59 nM; the half-blocking dose IC$_{50}$ of αO-GeXIVA14 was 34-96 nM; the half-blocking dose IC$_{50}$ of αO-GeXIVA13 was 106-232 nM. The half-blocking doses IC$_{50}$ of the 3 isomers to these 5 α9α10 nAChR mutants separately were: (1) rα9R71Gα10, αO-GeXIVA12, 59 nM; αO-GeXIVA13, 232 nM; αO-GeXIVA14, 61 nM; (2) α9S14Nα10, αO-GeXIVA12, 53 nM; αO-GeXIVA13, 108 nM; αO-GeXIVA14, 60 nM; (3) α9A24Kα10, αO-GeXIVA12, 52 nM; αO-GeXIVA13, 170 nM; αO-GeXIVA14, 96 nM; (4) α9E192Qα10, αO-GeXIVA12, 50 nM; αO-GeXIVA13, 143 nM; αO-GeXIVA14, 63 nM; (5) α9S136Nα10, αO-GeXIVA12, 46 nM; αO-GeXIVA13, 106 nM; αO-GeXIVA14, 34 nM.

There were 6 mutants having very small change of activity, the half-blocking dose IC$_{50}$ of αO-GeXIVA12 was 14-32 nM; the half-blocking dose IC$_{50}$ of αO-GeXIVA14 was 24-55 nM; the half-blocking dose IC$_{50}$ of αO-GeXIVA13 was 68-182 nM. As for 2 mutants, rα9S136Nα10 and rα9α10E56S, the blocking activity order of the 3 isomers was αO-GeXIVA14≥GeXIVA12>GeXIVA13. As for rα9S136Nα10 mutant, αO-GeXIVA14 (IC$_{50}$, 34 nM) showed stronger blocking activity than GeXIVA12 (IC$_{50}$, 46 nM). The half-blocking dose IC$_{50}$ of the 3 isomers to these 6 α9α10 nAChR mutants separately were: (1) rα9S117Aα10, αO-GeXIVA12, 32 nM; αO-GeXIVA13, 182 nM; αO-GeXIVA14, 47 nM; (2) αα10D116L, αO-GeXIVA12, 28 nM; αO-GeXIVA13, 122 nM; αO-GeXIVA14, 45 nM; (3) α9α10E56S, αO-GeXIVA12, 25 nM; αO-GeXIVA13, 68 nM; αO-GeXIVA14, 24 nM; (4) α9T56Iα10, αO-GeXIVA12, 23 nM; αO-GeXIVA13, 76 nM; αO-GeXIVA14, 33 nM; (5) α9S6Nα10, αO-GeXIVA12, 20 nM; αO-GeXIVA13, 119 nM; αO-GeXIVA14, 55 nM; (6) α9T64Iα10, αO-GeXIVA12, 14 nM; αO-GeXIVA13, 79 nM; αO-GeXIVA14, 24 nM.

The mutation sites of these α9α10 nAChR mutants were key amino acids of the receptor that were previously found to bind to α-conotoxin (Ellison M, Feng Z P, Park A J, Zhang X, Olivera B M, McIntosh J M, Norton R S. Alpha-RgIA, a novel conotoxin that blocks the alpha9alpha10 nAChR: structure and identification of key receptor-binding residues. J Mol Biol. 2008; 377(4):1216-27), the 3 isomers of αO-GeXIVA had not significant influence on activities of these mutants, i.e., their activity changes were about 10 or less times that of wild type α9α10 nAChR. This indicated that the binding sites or parts of αO-GeXIVA to α9α10 nAChR were totally different from those previously disclosed binding sites, i.e., they were new action sites.

Example 10

Novel Sites of αO-Conotoxin GeXIVA12 Specifically Blocking α9α10 nAChR

The elution of αO-GeXIVA12 blocking α9α10 nAChR was very fast (FIG. 9A). α-CTx RgIA [S4T; R9Cit; Y10Iodo, R11Q] (or RgIAM for short) was a specific blocking agent for α9α10 nAChR, but its elution was recovered very slowly (confirmed with experiment), that was, when toxin RgIAM was eluted, α9α10 nAChR restored very slowly to ACh normal gating open state (FIG. 9B).

Figure 9:
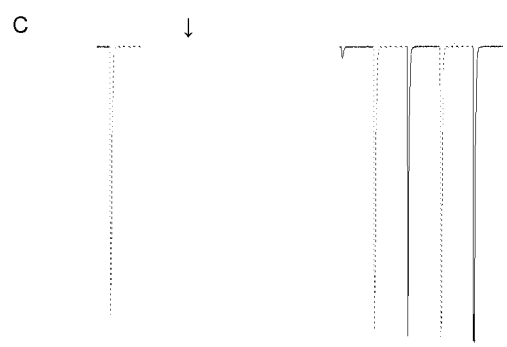
FIG. 9A-9C show that after αO-GeXIVA12 blocks α9α10 nAChR, the blocking effect of α-CTx RgIA [S4T; R9Cit; Y10Iodo, R11Q] on α9α10 nAChR can not be interrupted, which confirms that they bind to α9α10 nAChR at different sites. A. The arrow points at adminstration of 1 μM αO-GeXIVA12 at 5 min; B. The arrow points at administration of 20 nM α-CTx RgIA [S4T; R9Cit; Y10Iodo, R11Q] at 5 min; C. The arrow points at administration of 1 μM αO-GeXIVA12 1 min+[1 μM αO-GeXIVA12α20 nM α-CTx RgIA [S4T; R9Cit; Y10Iodo, R11Q] at 5 min].
Figure 9:
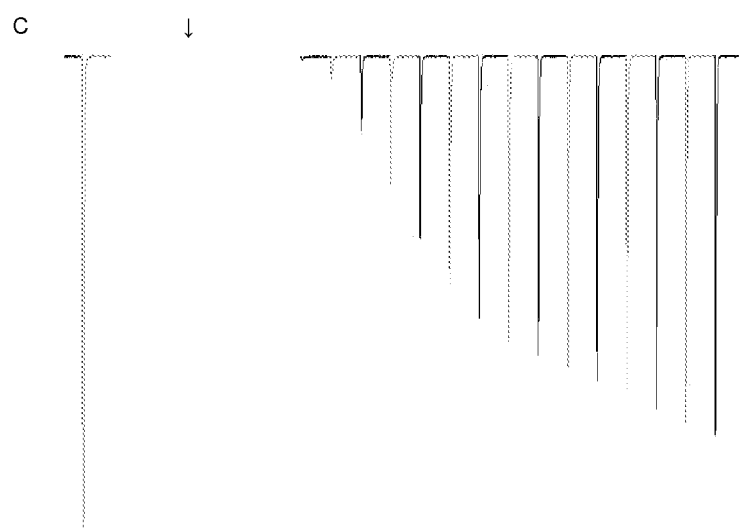
Figure 9:
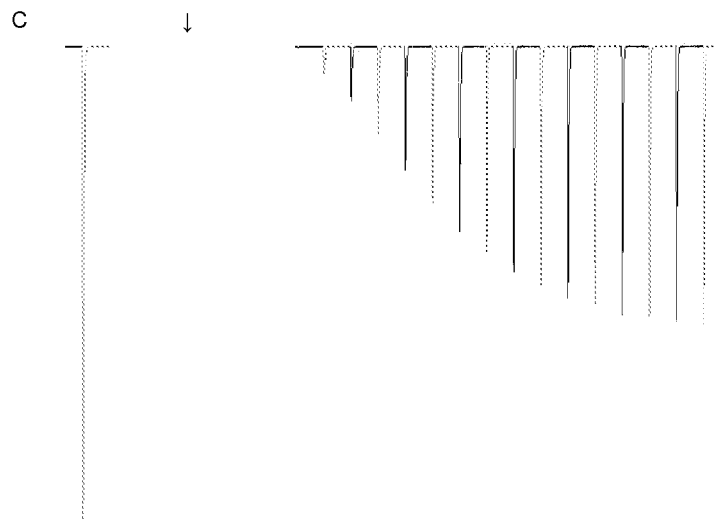

According to the different elution rates of the two, the inventors of the present invention designed a competitive test (FIG. 9C). That was, after incubation with 1 μM αO-GeXIVA12 to block α9α10 nAChR for 1 min, 20 nM α-CTx RgIAM and 1 μM αO-GeXIVA12 were then used in the same cell tank of frogspawn to continue incubation for blocking α9α10 nAChR 5 min, Ach gating current record showed its elution rate was very slow, and this was the same situation of solely using 20 nM α-CTx RgIAM for elution. In the meantime, it was set to use ND96 to separately replace αO-GeXIVA12 and α-CTx RgIAM, as positive and negative controls. The results showed that αO-GeXIVA12 could not inhibit the blocking activity of α-CTx RgIA M to α9α10 nAChR, which confirmed that the binding sites of the two to α9α10 nAChR were totally different, αO-conotoxin GeXIVA12 bound to novel sites of α9α10 nAChR, which were different from the previously disclosed binding sites of α-conotoxin, and not overlapped.

The studying showed that α9α10 nAChR were new target for treatment of neuralgia, chemical therapy of cancers, breast cancer, lung cancer, wound healing (McIntosh, J. M.; Absalom, N.; Chebib, M.; Elgoyhen, A. B.; Vincler, M., Alpha9 nicotinic acetylcholine receptors and the treatment of pain. *Biochemical pharmacology* 2009, 78 (7), 693-702.

Satkunanathan, N.; Livett, B.; Gayler, K.; Sandall, D.; Down, J.; Khalil, Z., Alpha-conotoxin Vc1.1 alleviates neuropathic pain and accelerates functional recovery of injured neurones. *Brain research* 2005, 1059 (2), 149-58. Holtman, J. R.; Dwoskin, L. P.; Dowell, C.; Wala, E. P.; Zhang, Z.; Crooks, P. A.; McIntosh, J. M., The novel small molecule alpha9alpha10 nicotinic acetylcholine receptor antagonist ZZ-204G is analgesic. *European journal of pharmacology* 2011, 670 (2-3), 500-8. Zheng, G.; Zhang, Z.; Dowell, C.; Wala, E.; Dwoskin, L. P.; Holtman, J. R.; McIntosh, J. M.; Crooks, P. A., Discovery of non-peptide, small molecule antagonists of alpha9alpha10 nicotinic acetylcholine receptors as novel analgesics for the treatment of neuropathic and tonic inflammatory pain. *Bioorganic & medicinal chemistry letters* 2011, 21 (8), 2476-9. Chernyaysky, A. I.; Arredondo, J.; Vetter, D. E.; Grando, S. A., Central role of alpha9 acetylcholine receptor in coordinating keratinocyte adhesion and motility at the initiation of epithelialization. *Experimental cell research* 2007, 313 (16), 3542-55; Chikova, A.; Grando, S. A., Naturally occurring variants of human Alpha9 nicotinic receptor differentially affect bronchial cell proliferation and transformation. *PloS one* 2011, 6 (11), e27978.). Hence, the new αO-superfamily conotoxin GeXIVA of the present invention is very promising in mechanism studying, diagnosis, and treatment of the above diseases.

Example 11

Experiment of Recombinant αO-Conotoxin GeXIVAWT Inhibiting Sf9 Cell Growth

Figure 10:
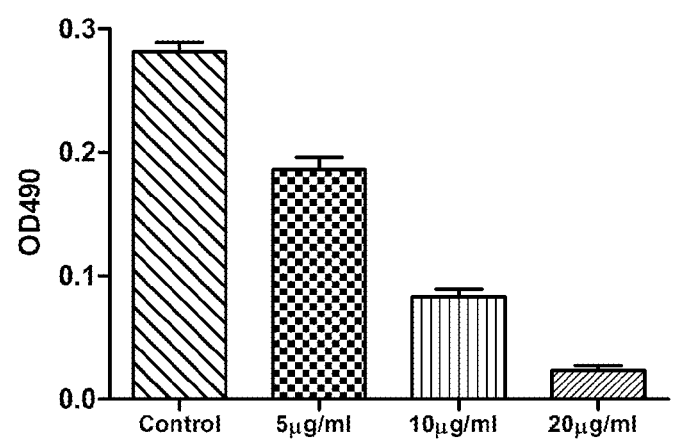
FIG. 10: shows the inhibition effects of a recombinant αO-superfamily conotoxin wild type GeXIVAWT (rCTx-K41) on Sf9 cells, in which abscissa is concentration of recombinant GeXIVAWT with unit of μg/ml, Control is a negative control without adding recombinant GeXIVAWT; ordinate is optical absorbance value measured with an enzyme-labeled immunoassay instrument (BIO-RAD MODEL 550) under 490 nm wavelength.

The gene of wild type toxin (αO-GeXIVAWT) was inserted into between restriction enzyme cutting sites Nco I and Xho I of *E. coli* expression vector pET22b(+), to construct a fusion protein expression vector which N-terminal fused with pelB leader and C-terminal fused with His-tag purification label. The αO-GeXIVAWT recombinant protein was separated and purified. The effects of the recombinant conotoxin αO-GeXIVAWT on the growth state of Sf9 cells (*Spodoptera frugiperda* 9 (Sf9) cells, purchased from Invitrogen Company of USA) was studied by MTT method (FIG. 10). The method was carried out according to that MTT could penetrated cell membrane and entered into cell, succinate dehydrogenase in a living cell mitochondria could reduce exogenous MTT into water-insoluble needle-like blue-purple formazane crystal which precipitated in the cell, while dead cell had not such function. Dimethylsulfoxide (DMSO) could dissolve the blue-purple crystal in cell, and the intensity of color of the resultant solution was in direct proportion to the contained formazane content. Its optical density value (OD value) was measured under wavelength of 570 nm with ELIASA, and could indirectly reflect number of cells. The results showed that αO-GeXIVAWT could significantly inhibit growth of Sf9 cells, had dose effect, and could kill Sf9 cells under high concentration (>10 μg/ml). Sf-9 insect cell line was from ovary cell line Sf-21 of agricultural insect *Spodoptera Frugiperda*, this insect cell was very prone to infection with alfalfa California nuclear polyhedrosis virus (AcMNPV baculovirus) as biopesticide, and could be used as expression vector for all baculovirus. Hence, the wild type recombinant conotoxin αO-GeXIVAWT was promising in pest control (Bruce C, Fitches E C, Chougule N, Bell H A, Gatehouse J A (2011) Recombinant conotoxin, TxVIA, produced in yeast has insecticidal activity. Toxicon 58:93-100.).

Although the embodiments of the present invention are described in details, those skilled in the art would understand that these details could be modified and changed according to the disclosed teachings, and all these changes fall into the protection scope of the present invention. The whole scope of the present invention is given by the appended claims and any equivalents thereof.

What is claimed is:

1. A polypeptide, which consists of or comprises one or more same or different amino acid sequences as shown by any one of SEQ ID NOs: 10-12.

2. A polypeptide according to claim 1, wherein the polypeptide consists of or comprises SEQ ID NO: 12, wherein from the N-terminus of SEQ ID NO:12, the $1^{st}$ cysteine and the $2^{nd}$ cysteine form a disulfide bond, and the $3^{rd}$ cysteine and the $4^{th}$ cysteine form a disulfide bond; or the $1^{st}$ cysteine and the $3^{rd}$ cysteine form a disulfide bond, and the $2^{nd}$ cysteine and the $4^{th}$ cysteine form a disulfide bond; or the $1^{st}$ cysteine and the $4^{th}$ cysteine form a disulfide bond, and the $2^{nd}$ cysteine and the $3^{rd}$ cysteine form a disulfide bond; and the carboxyl terminus of the polypeptide is a free C-terminus, or amidated.

3. A fusion protein, which comprises a polypeptide according to claim 1.

4. A pharmaceutical composition, which comprises a polypeptide according to claim 1.

5. A method for preparing a polypeptide according to claim 1, comprising the following steps:
   1) synthesizing a linear polypeptide by ABI Prism 433a polypeptide synthesizer or by a manual method, in which side-chain protecting groups of Fmoc amino acid are: Pmc (Arg), Trt (Cys), But (Thr, Ser, Tyr), OBut (Asp), Boc (Lys); cysteine is protected with Trt or Acm protecting group, disulfide bonds are respectively formed in a site-directed manner between corresponding cysteines;
   2) cutting the linear polypeptide of step 1) from resin, using ice-ether to precipitate and wash and recover a crude product of the linear polypeptide, and using a preparative reversed phase HPLC C18 column for purification; and
   3) subjecting the product obtained in step 2) to two-step oxidative folding.

6. A method for treatment and/or prophylaxis of neuralgia, breast cancer, or lung cancer a method for killing a pest, or a method for analgesia, comprising the step of administering an effective amount of a polypeptide according to claim 1.

7. The pharmaceutical composition according to claim 4, which further comprises a pharmaceutically acceptable carrier or an excipient.

8. The method according to claim 6, wherein said pest is *Spodoptera Frugiperda*.

9. The method according to claim 6, wherein said neuralgia is caused by a factor selected from: cancers and chemotherapy of cancers, alcoholism, ischioneuralgia, diabetes mellitus, prosopalgia, sclerosis, herpes zoster, mechanical injury and surgical injury, AIDS, head nerve paralysis, drug poisoning, industrial pollution poisoning, lymphatic neuralgia, myeloma, multipoint motor neuralgia, chronic congenital esthesioneurosis, acute spontaneous neuralgia, squeezing neuralgia, angiitis, vasculitis, ischemia, uremia, children biliary liver disease, chronic respiratory disorder, complex neuralgia, multiple organ failure, sepsis/pyaemia, hepatitis, *porphyria*, avitaminosis, chronic liver diseases, primary biliary cirrhosis, hyperlipidemia, leprosy, Lyme arthritis, sensory perineuritis, and allergies.

10. The method according to claim 6, wherein said treatment is adjuvant treatment.

* * * * *

SEQUENCE LISTING

<160> NUMBER OF SEQ ID NOS: 37

<210> SEQ ID NO 1
<211> LENGTH: 225
<212> TYPE: DNA
<213> ORGANISM: Conus generalis

<400> SEQUENCE: 1

```
atgaaactga cgtgcgtgtt gatcatcacc gtgctgttcc tgacggcctg tcaactcact      60
acagctgtga cttactccag aggtgagcat aagcatcgtg ctctgatgtc aactggcaca     120
aactacaggt tgcccaagac gtgccgtagt tccggtcgtt attgtcgctc accttatgat     180
tgccgcagaa gatattgcag acgcattacg gatgcgtgcg tatag                      225
```

<210> SEQ ID NO 2
<211> LENGTH: 225
<212> TYPE: DNA
<213> ORGANISM: Conus generalis

<400> SEQUENCE: 2

```
atgaaactga cgtgcgtggt gatcatcacc gtgctgttcc tgacggcctg tcaactcact      60
acagctgtga cttactccag aggtgagcat aagcatcgtg ctctgatgtc aactggcaca     120
aactacaggt tgcccaagac gtgccgtagt tccggtcgtt attgtcgctc accttatgat     180
```

```
tgccgcagaa gatattgcag acgcattacg gatgcgtgcg tatag          225

<210> SEQ ID NO 3
<211> LENGTH: 87
<212> TYPE: DNA
<213> ORGANISM: Conus generalis

<400> SEQUENCE: 3
acgtgccgta gttccggtcg ttattgtcgc tcaccttatg attgccgcag aagatattgc    60
agacgcatta cggatgcgtg cgtatag                                        87

<210> SEQ ID NO 4
<211> LENGTH: 225
<212> TYPE: DNA
<213> ORGANISM: Artificial
<220> FEATURE:
<223> OTHER INFORMATION: Synthetic polynucleotide

<400> SEQUENCE: 4
atgaaactga cgtgcgtgtt gatcatcacc gtgctgttcc tgacggcctg tcaactcact    60
acagctgtga cttactccag aggtgagcat aagcatcgtg ctctgatgtc aactggcaca   120
aactacaggt tgcccaagac gtgccgtagt tccggtcgtt attgtcgctc accttatgat   180
cgccgcagaa gatattgcag acgcattacg gatgcgtgcg tatag                   225

<210> SEQ ID NO 5
<211> LENGTH: 225
<212> TYPE: DNA
<213> ORGANISM: Artificial
<220> FEATURE:
<223> OTHER INFORMATION: Synthetic polynucleotide

<400> SEQUENCE: 5
atgaaactga cgtgcgtggt gatcatcacc gtgctgttcc tgacggcctg tcaactcact    60
acagctgtga cttactccag aggtgagcat aagcatcgtg ctctgatgtc aactggcaca   120
aactacaggt tgcccaagac gtgccgtagt tccggtcgtt attgtcgctc accttatgat   180
cgccgcagaa gatattgcag acgcattacg gatgcgtgcg tatag                   225

<210> SEQ ID NO 6
<211> LENGTH: 87
<212> TYPE: DNA
<213> ORGANISM: Artificial
<220> FEATURE:
<223> OTHER INFORMATION: Synthetic polynucleotide

<400> SEQUENCE: 6
acgtgccgta gttccggtcg ttattgtcgc tcaccttatg atcgccgcag aagatattgc    60
agacgcatta cggatgcgtg cgtatag                                        87

<210> SEQ ID NO 7
<211> LENGTH: 74
<212> TYPE: PRT
<213> ORGANISM: Conus generalis

<400> SEQUENCE: 7

Met Lys Leu Thr Cys Val Leu Ile Ile Thr Val Leu Phe Leu Thr Ala
1               5                  10                  15

Cys Gln Leu Thr Thr Ala Val Thr Tyr Ser Arg Gly Glu His Lys His
            20                  25                  30

Arg Ala Leu Met Ser Thr Gly Thr Asn Tyr Arg Leu Pro Lys Thr Cys
```

```
                   35                  40                  45

Arg Ser Ser Gly Arg Tyr Cys Arg Ser Pro Tyr Asp Cys Arg Arg
    50                  55                  60

Tyr Cys Arg Arg Ile Thr Asp Ala Cys Val
65                  70

<210> SEQ ID NO 8
<211> LENGTH: 74
<212> TYPE: PRT
<213> ORGANISM: Conus generalis

<400> SEQUENCE: 8

Met Lys Leu Thr Cys Val Val Ile Ile Thr Val Leu Phe Leu Thr Ala
1               5                   10                  15

Cys Gln Leu Thr Thr Ala Val Thr Tyr Ser Arg Gly Glu His Lys His
                20                  25                  30

Arg Ala Leu Met Ser Thr Gly Thr Asn Tyr Arg Leu Pro Lys Thr Cys
            35                  40                  45

Arg Ser Ser Gly Arg Tyr Cys Arg Ser Pro Tyr Asp Cys Arg Arg
    50                  55                  60

Tyr Cys Arg Arg Ile Thr Asp Ala Cys Val
65                  70

<210> SEQ ID NO 9
<211> LENGTH: 28
<212> TYPE: PRT
<213> ORGANISM: Conus generalis

<400> SEQUENCE: 9

Thr Cys Arg Ser Ser Gly Arg Tyr Cys Arg Ser Pro Tyr Asp Cys Arg
1               5                   10                  15

Arg Arg Tyr Cys Arg Arg Ile Thr Asp Ala Cys Val
                20                  25

<210> SEQ ID NO 10
<211> LENGTH: 74
<212> TYPE: PRT
<213> ORGANISM: Artificial
<220> FEATURE:
<223> OTHER INFORMATION: Synthetic peptide

<400> SEQUENCE: 10

Met Lys Leu Thr Cys Val Leu Ile Ile Thr Val Leu Phe Leu Thr Ala
1               5                   10                  15

Cys Gln Leu Thr Thr Ala Val Thr Tyr Ser Arg Gly Glu His Lys His
                20                  25                  30

Arg Ala Leu Met Ser Thr Gly Thr Asn Tyr Arg Leu Pro Lys Thr Cys
            35                  40                  45

Arg Ser Ser Gly Arg Tyr Cys Arg Ser Pro Tyr Asp Arg Arg Arg
    50                  55                  60

Tyr Cys Arg Arg Ile Thr Asp Ala Cys Val
65                  70

<210> SEQ ID NO 11
<211> LENGTH: 74
<212> TYPE: PRT
<213> ORGANISM: Artificial
<220> FEATURE:
<223> OTHER INFORMATION: Synthetic peptide

<400> SEQUENCE: 11
```

```
Met Lys Leu Thr Cys Val Val Ile Ile Thr Val Leu Phe Leu Thr Ala
1               5                   10                  15

Cys Gln Leu Thr Thr Ala Val Thr Tyr Ser Arg Gly Glu His Lys His
            20                  25                  30

Arg Ala Leu Met Ser Thr Gly Thr Asn Tyr Arg Leu Pro Lys Thr Cys
        35                  40                  45

Arg Ser Ser Gly Arg Tyr Cys Arg Ser Pro Tyr Asp Arg Arg Arg
    50                  55                  60

Tyr Cys Arg Arg Ile Thr Asp Ala Cys Val
65                  70
```

<210> SEQ ID NO 12
<211> LENGTH: 28
<212> TYPE: PRT
<213> ORGANISM: Artificial
<220> FEATURE:
<223> OTHER INFORMATION: Synthetic peptide

<400> SEQUENCE: 12

```
Thr Cys Arg Ser Ser Gly Arg Tyr Cys Arg Ser Pro Tyr Asp Arg Arg
1               5                   10                  15

Arg Arg Tyr Cys Arg Arg Ile Thr Asp Ala Cys Val
            20                  25
```

<210> SEQ ID NO 13
<211> LENGTH: 24
<212> TYPE: DNA
<213> ORGANISM: Artificial
<220> FEATURE:
<223> OTHER INFORMATION: Synthetic oligonucleotide

<400> SEQUENCE: 13
catcgtcaag atgaaactga cgtg                                            24

<210> SEQ ID NO 14
<211> LENGTH: 21
<212> TYPE: DNA
<213> ORGANISM: Artificial
<220> FEATURE:
<223> OTHER INFORMATION: Synthetic oligonucleotide

<400> SEQUENCE: 14
cacaggtatg gatgactcag g                                               21

<210> SEQ ID NO 15
<211> LENGTH: 75
<212> TYPE: PRT
<213> ORGANISM: Artificial Sequence
<220> FEATURE:
<223> OTHER INFORMATION: Synthetic peptide

<400> SEQUENCE: 15

```
Met Lys Leu Thr Cys Val Leu Val Ile Ile Thr Val Leu Phe Leu Thr
1               5                   10                  15

Ala Cys Gln Leu Thr Thr Ala Val Thr Tyr Ser Arg Gly Glu His Lys
            20                  25                  30

His Arg Ala Leu Met Ser Thr Gly Thr Asn Tyr Arg Leu Pro Lys Thr
        35                  40                  45

Cys Arg Ser Ser Gly Arg Tyr Cys Arg Ser Pro Tyr Asp Cys Arg Arg
    50                  55                  60

Arg Tyr Cys Arg Arg Ile Thr Asp Ala Cys Val
```

-continued

```
            65                  70                  75

<210> SEQ ID NO 16
<211> LENGTH: 75
<212> TYPE: PRT
<213> ORGANISM: Artificial Sequence
<220> FEATURE:
<223> OTHER INFORMATION: Synthetic peptide

<400> SEQUENCE: 16

Met Lys Leu Thr Cys Val Leu Val Ile Ile Thr Val Leu Phe Leu Thr
1               5                   10                  15

Ala Cys Gln Leu Thr Thr Ala Val Thr Tyr Ser Arg Gly Glu His Lys
            20                  25                  30

His Arg Ala Leu Met Ser Thr Gly Thr Asn Tyr Arg Leu Pro Lys Thr
        35                  40                  45

Cys Arg Ser Ser Gly Arg Tyr Cys Arg Ser Pro Tyr Asp Arg Arg Arg
    50                  55                  60

Arg Tyr Cys Arg Arg Ile Thr Asp Ala Cys Val
65                  70                  75

<210> SEQ ID NO 17
<211> LENGTH: 71
<212> TYPE: PRT
<213> ORGANISM: Artificial Sequence
<220> FEATURE:
<223> OTHER INFORMATION: Synthetic peptide

<400> SEQUENCE: 17

Met Lys Leu Thr Cys Val Val Ile Val Ala Val Leu Leu Leu Thr Ala
1               5                   10                  15

Cys Gln Leu Ile Thr Ala Asp Asp Ser Arg Gly Thr Gln Lys His Arg
            20                  25                  30

Ala Leu Arg Ser Thr Thr Lys Leu Ser Thr Ser Thr Arg Cys Lys Gly
        35                  40                  45

Lys Gly Ala Lys Cys Ser Arg Leu Met Tyr Asp Cys Cys Thr Gly Ser
    50                  55                  60

Cys Arg Ser Gly Lys Cys Gly
65                  70

<210> SEQ ID NO 18
<211> LENGTH: 76
<212> TYPE: PRT
<213> ORGANISM: Artificial Sequence
<220> FEATURE:
<223> OTHER INFORMATION: Synthetic peptide

<400> SEQUENCE: 18

Met Glu Lys Leu Thr Ile Leu Leu Leu Val Ala Ala Val Leu Met Ser
1               5                   10                  15

Thr Gln Ala Leu Ile Gln Ser Asp Gly Glu Lys Arg Gln Gln Ala Lys
            20                  25                  30

Ile Asn Phe Leu Ser Arg Lys Ser Thr Ala Glu Ser Trp Trp Glu Gly
        35                  40                  45

Glu Cys Lys Gly Trp Ser Val Tyr Cys Ser Trp Asp Trp Glu Cys Cys
    50                  55                  60

Ser Gly Glu Cys Thr Arg Tyr Tyr Cys Glu Leu Trp
65                  70                  75

<210> SEQ ID NO 19
```

<211> LENGTH: 78
<212> TYPE: PRT
<213> ORGANISM: Artificial Sequence
<220> FEATURE:
<223> OTHER INFORMATION: Synthetic peptide

<400> SEQUENCE: 19

Met Ser Gly Leu Gly Ile Met Val Leu Thr Leu Leu Leu Leu Val Phe
1               5                   10                  15

Met Glu Ala Ser His Gln Asp Ala Gly Glu Lys Gln Ala Thr Gln Arg
            20                  25                  30

Asp Ala Ile Asn Val Arg Arg Arg Ser Leu Ala Arg Arg Thr Val
        35                  40                  45

Thr Glu Glu Cys Glu Glu Asp Cys Glu Asp Glu Lys His Cys Cys
50                  55                  60

Asn Thr Asn Asn Gly Pro Ser Cys Ala Arg Leu Cys Phe Gly
65                  70                  75

<210> SEQ ID NO 20
<211> LENGTH: 76
<212> TYPE: PRT
<213> ORGANISM: Artificial Sequence
<220> FEATURE:
<223> OTHER INFORMATION: Synthetic peptide

<400> SEQUENCE: 20

Met Pro Ser Val Arg Ser Val Thr Cys Cys Cys Leu Leu Trp Met Met
1               5                   10                  15

Phe Ser Val Gln Leu Val Thr Pro Gly Ser Pro Gly Thr Ala Gln Leu
            20                  25                  30

Ser Gly His Arg Thr Ala Arg Phe Pro Arg Pro Arg Ile Cys Asn Leu
        35                  40                  45

Ala Cys Arg Ala Gly Ile Gly His Lys Tyr Pro Phe Cys His Cys Arg
    50                  55                  60

Gly Lys Arg Asp Ala Val Ser Ser Met Ala Val
65                  70                  75

<210> SEQ ID NO 21
<211> LENGTH: 64
<212> TYPE: PRT
<213> ORGANISM: Artificial Sequence
<220> FEATURE:
<223> OTHER INFORMATION: Synethic peptide

<400> SEQUENCE: 21

Met Lys Leu Ser Val Met Phe Ile Val Phe Leu Met Leu Thr Met Pro
1               5                   10                  15

Met Thr Cys Ala Gly Ile Ser Arg Ser Ala Thr Asn Gly Gly Glu Ala
            20                  25                  30

Asp Val Arg Ala His Asp Lys Ala Ala Asn Leu Met Ala Leu Leu Gln
        35                  40                  45

Glu Arg Met Cys Pro Pro Leu Cys Lys Pro Ser Cys Thr Asn Cys Gly
    50                  55                  60

<210> SEQ ID NO 22
<211> LENGTH: 60
<212> TYPE: PRT
<213> ORGANISM: Artificial Sequence
<220> FEATURE:
<223> OTHER INFORMATION: Synthetic peptide

<400> SEQUENCE: 22

Met Phe Thr Val Phe Leu Leu Val Val Leu Thr Thr Val Val Ser
1               5                   10                  15

Phe Pro Ser Asp Arg Ala Ser Asp Gly Arg Asn Ala Ala Asn Asp
                20                  25                  30

Lys Ala Ser Asp Val Val Thr Leu Val Leu Lys Gly Cys Cys Ser Thr
            35                  40                  45

Pro Pro Cys Ala Val Leu Tyr Cys Gly Arg Arg
    50                  55                  60

<210> SEQ ID NO 23
<211> LENGTH: 68
<212> TYPE: PRT
<213> ORGANISM: Artificial Sequence
<220> FEATURE:
<223> OTHER INFORMATION: Synthetic peptide

<400> SEQUENCE: 23

Met Phe Thr Val Phe Leu Leu Val Val Leu Ala Thr Thr Val Val Ser
1               5                   10                  15

Phe Thr Ser Asp Arg Ala Ser Asp Asp Arg Asn Thr Asn Asp Lys Ala
                20                  25                  30

Ser Arg Leu Leu Ser His Val Val Arg Gly Cys Cys Gly Ser Tyr Pro
            35                  40                  45

Asn Ala Ala Cys His Pro Cys Ser Cys Lys Asp Arg Pro Ser Tyr Cys
    50                  55                  60

Gly Gln Gly Arg
65

<210> SEQ ID NO 24
<211> LENGTH: 85
<212> TYPE: PRT
<213> ORGANISM: Artificial sequence
<220> FEATURE:
<223> OTHER INFORMATION: Synthetic peptide

<400> SEQUENCE: 24

Met Gln Thr Ala Tyr Trp Val Met Val Met Met Val Met Trp Ile
1               5                   10                  15

Thr Ala Pro Leu Ser Glu Gly Gly Lys Pro Lys Leu Ile Ile Arg Gly
                20                  25                  30

Leu Val Pro Asn Asp Leu Thr Pro Gln Arg Ile Leu Arg Ser Leu Ile
            35                  40                  45

Ser Gly Arg Thr Tyr Gly Ile Tyr Asp Ala Lys Pro Pro Phe Ser Cys
    50                  55                  60

Ala Gly Leu Arg Gly Gly Cys Val Leu Pro Pro Asn Leu Arg Pro Lys
65                  70                  75                  80

Phe Lys Glu Gly Arg
                85

<210> SEQ ID NO 25
<211> LENGTH: 92
<212> TYPE: PRT
<213> ORGANISM: Artificial Sequence
<220> FEATURE:
<223> OTHER INFORMATION: Synthetic peptide

<400> SEQUENCE: 25

Met Pro Lys Leu Glu Met Met Leu Leu Val Leu Leu Ile Phe Pro Leu
1               5                   10                  15

```
Ser Tyr Phe Ile Ala Ala Gly Gly Gln Val Gln Val Asp Arg Arg
            20                  25                  30

Gly Asp Gly Leu Ala Gly Tyr Leu Gln Arg Gly Asp Arg Asp Val Gln
        35                  40                  45

Asp Cys Gln Val Ser Thr Pro Gly Ser Lys Trp Gly Arg Cys Cys Leu
50                  55                  60

Asn Arg Val Cys Gly Pro Met Cys Cys Pro Ala Ser His Cys Tyr Cys
65                  70                  75                  80

Val Tyr His Arg Gly Arg Gly His Gly Cys Ser Cys
                85                  90
```

<210> SEQ ID NO 26
<211> LENGTH: 93
<212> TYPE: PRT
<213> ORGANISM: Artificial Sequence
<220> FEATURE:
<223> OTHER INFORMATION: Synthetic peptide

<400> SEQUENCE: 26

```
Met Met Ser Lys Met Gly Ala Met Phe Val Leu Leu Leu Leu Phe Thr
1               5                   10                  15

Leu Ala Ser Ser Gln Gln Glu Gly Asp Val Gln Ala Arg Lys Thr His
            20                  25                  30

Pro Lys Arg Glu Phe Gln Arg Ile Leu Leu Arg Ser Gly Arg Lys Cys
        35                  40                  45

Asn Phe Asp Lys Cys Lys Gly Thr Gly Val Tyr Asn Cys Gly Glu Ser
50                  55                  60

Cys Ser Cys Glu Gly Leu His Ser Cys Arg Cys Thr Tyr Asn Ile Gly
65                  70                  75                  80

Ser Met Lys Ser Gly Cys Ala Cys Ile Cys Thr Tyr Tyr
                85                  90
```

<210> SEQ ID NO 27
<211> LENGTH: 28
<212> TYPE: PRT
<213> ORGANISM: C. generalis

<400> SEQUENCE: 27

```
Thr Cys Arg Ser Ser Gly Arg Tyr Cys Arg Ser Pro Tyr Asp Arg Arg
1               5                   10                  15

Arg Arg Tyr Cys Arg Arg Ile Thr Asp Ala Cys Val
            20                  25
```

<210> SEQ ID NO 28
<211> LENGTH: 25
<212> TYPE: PRT
<213> ORGANISM: C. magus
<220> FEATURE:
<221> NAME/KEY: MOD_RES
<222> LOCATION: (25)..(25)
<223> OTHER INFORMATION: AMIDATION

<400> SEQUENCE: 28

```
Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25
```

<210> SEQ ID NO 29
<211> LENGTH: 25
<212> TYPE: PRT

```
<213> ORGANISM: C. planorbis
<220> FEATURE:
<221> NAME/KEY: MOD_RES
<222> LOCATION: (25)..(25)
<223> OTHER INFORMATION: AMIDATION

<400> SEQUENCE: 29

Phe Pro Arg Pro Arg Ile Cys Asn Leu Ala Cys Arg Ala Gly Ile Gly
1               5                   10                  15
His Lys Tyr Pro Phe Cys His Cys Arg
            20                  25

<210> SEQ ID NO 30
<211> LENGTH: 13
<212> TYPE: PRT
<213> ORGANISM: C. litteratus
<220> FEATURE:
<221> NAME/KEY: MOD_RES
<222> LOCATION: (13)..(13)
<223> OTHER INFORMATION: AMIDATION

<400> SEQUENCE: 30

Met Cys Pro Pro Leu Cys Lys Pro Ser Cys Thr Asn Cys
1               5                   10

<210> SEQ ID NO 31
<211> LENGTH: 27
<212> TYPE: PRT
<213> ORGANISM: C. Villepinii

<400> SEQUENCE: 31

Gly Gly Leu Gly Arg Cys Ile Tyr Asn Cys Met Asn Ser Gly Gly
1               5                   10                  15
Leu Ser Phe Ile Gln Cys Lys Thr Met Cys Tyr
            20                  25

<210> SEQ ID NO 32
<211> LENGTH: 24
<212> TYPE: PRT
<213> ORGANISM: C. purpurascens
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MOD_RES
<222> LOCATION: (24)..(24)
<223> OTHER INFORMATION: AMIDATION

<400> SEQUENCE: 32

His Xaa Xaa Cys Cys Leu Tyr Gly Lys Cys Arg Arg Tyr Xaa Gly Cys
1               5                   10                  15
Ser Ser Ala Ser Cys Cys Gln Arg
            20

<210> SEQ ID NO 33
<211> LENGTH: 16
<212> TYPE: PRT
<213> ORGANISM: C.litteratus
<220> FEATURE:
<221> NAME/KEY: MOD_RES
<222> LOCATION: (16)..(16)
<223> OTHER INFORMATION: AMIDATION
```

```
<400> SEQUENCE: 33

Gly Cys Cys Ala Arg Ala Ala Cys Ala Gly Ile His Gln Glu Leu Cys
1               5                   10                  15

<210> SEQ ID NO 34
<211> LENGTH: 30
<212> TYPE: PRT
<213> ORGANISM: C. ermineus
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: MOD_RES
<222> LOCATION: (30)..(30)
<223> OTHER INFORMATION: AMIDATION

<400> SEQUENCE: 34

Gly Cys Cys Gly Pro Tyr Xaa Asn Ala Ala Cys His Xaa Cys Gly Cys
1               5                   10                  15

Lys Val Gly Arg Xaa Xaa Tyr Cys Asp Arg Xaa Ser Gly Gly
            20                  25                  30

<210> SEQ ID NO 35
<211> LENGTH: 32
<212> TYPE: PRT
<213> ORGANISM: C. parius
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: MOD_RES
<222> LOCATION: (32)..(32)
<223> OTHER INFORMATION: AMIDATION

<400> SEQUENCE: 35

Thr Tyr Gly Ile Tyr Asp Ala Lys Pro Xaa Phe Ser Cys Ala Gly Leu
1               5                   10                  15

Arg Gly Gly Cys Val Leu Pro Xaa Asn Leu Arg Xaa Lys Phe Lys Glu
            20                  25                  30

<210> SEQ ID NO 36
<211> LENGTH: 48
<212> TYPE: PRT
<213> ORGANISM: C. vexillum

<400> SEQUENCE: 36

Asp Asp Ser Cys Ile Ile Asn Thr Arg Asp Ser Pro Trp Gly Arg Cys
1               5                   10                  15
```

```
Cys Arg Thr Arg Met Cys Gly Ser Met Cys Cys Pro Arg Asn Gly Cys
            20                  25                  30

Thr Cys Val Tyr His Trp Arg Arg Gly His Gly Cys Ser Cys Pro Gly
            35                  40                  45

<210> SEQ ID NO 37
<211> LENGTH: 45
<212> TYPE: PRT
<213> ORGANISM: C.radiatus

<400> SEQUENCE: 37

Lys Cys Asn Phe Asp Lys Cys Lys Gly Thr Gly Val Tyr Asn Cys Gly
1               5                   10                  15

Ser Cys Ser Cys Gly Leu His Ser Cys Arg Cys Thr Tyr Asn Ile Gly
            20                  25                  30

Ser Met Lys Ser Gly Cys Ala Cys Ile Cys Thr Tyr Tyr
            35                  40                  45
```